US 11,439,295 B2

(12) United States Patent
Hosogoe et al.

(10) Patent No.: US 11,439,295 B2
(45) Date of Patent: Sep. 13, 2022

(54) ENDOSCOPE CAP, ENDOSCOPE AND METHOD OF DETACHING ENDOSCOPE CAP

(71) Applicant: HOYA CORPORATION, Tokyo (JP)

(72) Inventors: Yoshitsugu Hosogoe, Tokyo (JP); Keiichi Saito, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 526 days.

(21) Appl. No.: 16/326,142

(22) PCT Filed: Oct. 13, 2017

(86) PCT No.: PCT/JP2017/037108
§ 371 (c)(1),
(2) Date: Feb. 15, 2019

(87) PCT Pub. No.: WO2018/070508
PCT Pub. Date: Apr. 19, 2018

(65) Prior Publication Data
US 2019/0223698 A1 Jul. 25, 2019

(30) Foreign Application Priority Data
Oct. 14, 2016 (JP) .............................. JP2016-202919

(51) Int. Cl.
A61B 1/00 (2006.01)
A61B 1/018 (2006.01)

(52) U.S. Cl.
CPC ...... A61B 1/00137 (2013.01); A61B 1/00089 (2013.01); A61B 1/00098 (2013.01); A61B 1/00101 (2013.01); A61B 1/018 (2013.01)

(58) Field of Classification Search
CPC ............ A61B 1/00098; A61B 1/00101; A61B 1/00135; A61B 1/00137; A61B 1/00142;
(Continued)

(56) References Cited

U.S. PATENT DOCUMENTS 5,562,600 A 10/1996 Matsuno
5,569,157 A * 10/1996 Nakazawa ............. A61B 1/018
600/106
(Continued)

FOREIGN PATENT DOCUMENTS

CN 101061940 A 10/2007
CN 105982635 A 10/2016
(Continued)

OTHER PUBLICATIONS

PCT/JP2017/037108, "English translation of International Search Report", dated Dec. 26, 2017.
(Continued)

Primary Examiner — Ryan N Henderson
(74) Attorney, Agent, or Firm — Kilpatrick Townsend & Stockton LLP

(57) ABSTRACT

An example endoscope cap attachable to and detachable from an endoscope including a lever pivotally provided at a distal end of an insertion part of an endoscope and a pivot part causing the lever to pivot, includes: a bottomed cylindrical cover having an opening end which is attachable to and detachable from a distal end of an insertion part of the endoscope; a first engagement part provided at an inner surface of a cylindrical part of the cover; and an elevator having a lever connection part connected to the lever and pivotally fixed to an inside of the cover.

10 Claims, 26 Drawing Sheets

(58) Field of Classification Search
CPC ... A61B 1/00181; A61B 1/018; A61B 1/0008; G02B 23/24; G02B 23/2476

See application file for complete search history.

(56) References Cited

U.S. PATENT DOCUMENTS

| | | | |
|---|---|---|---|
| 5,868,663 | A | 2/1999 | Katsurada et al. |
| 10,856,724 | B2* | 12/2020 | Miller ............. A61B 1/00098 |
| 11,019,984 | B2* | 6/2021 | Miller ............. A61B 1/00137 |
| 2007/0246506 | A1 | 10/2007 | Hamazaki et al. |
| 2007/0270638 | A1 | 11/2007 | Kitano et al. |
| 2016/0227988 | A1 | 8/2016 | Jiang et al. |
| 2016/0270635 | A1 | 9/2016 | Tanaka et al. |
| 2016/0270636 | A1 | 9/2016 | Iwasaka et al. |
| 2016/0270637 | A1* | 9/2016 | Tanaka ............. A61B 1/00098 |
| 2017/0000319 | A1* | 1/2017 | Iizuka ............... A61B 1/018 |
| 2017/0238789 | A1* | 8/2017 | Iizuka ............... A61B 1/018 |
| 2018/0206708 | A1* | 7/2018 | Miller ............. A61B 1/00133 |
| 2018/0249894 | A1* | 9/2018 | Kolberg ........... A61B 1/00137 |
| 2018/0279857 | A1* | 10/2018 | Miller ............. A61B 1/00098 |
| 2019/0223697 | A1* | 7/2019 | Hosogoe ......... A61B 1/00101 |
| 2019/0223698 | A1* | 7/2019 | Hosogoe ......... A61B 1/00137 |
| 2020/0178767 | A1* | 6/2020 | Miller ............. A61B 1/00131 |
| 2020/0178773 | A1* | 6/2020 | Miller ............. A61B 1/00101 |
| 2020/0337530 | A1* | 10/2020 | Miller ............. A61B 1/00165 |

FOREIGN PATENT DOCUMENTS

| | | |
|---|---|---|
| JP | H06-315458 | 11/1994 |
| JP | H08-056900 | 3/1996 |
| JP | H08-071032 | 3/1996 |
| JP | H08-126605 | 5/1996 |
| JP | H08-243071 | 9/1996 |
| JP | H08-243076 | 9/1996 |
| JP | H08-252211 | 10/1996 |
| JP | H09-253036 | 9/1997 |
| JP | H11-004804 | 1/1999 |
| JP | 2002-017655 | 1/2002 |
| JP | 2004-267596 | 9/2004 |
| JP | 2007-330756 | 12/2007 |
| JP | 2009-273665 | 11/2009 |
| JP | 2009-284939 | 12/2009 |
| JP | 2013-039358 | 2/2013 |
| JP | 2016-174821 | 10/2016 |
| JP | 2016-174822 | 10/2016 |

OTHER PUBLICATIONS

PCT/JP2017/037111, "English translation of International Search Report", dated Dec. 5, 2017.
PCT/JP2017/037177, "English translation of International Search Report", dated Dec. 26, 2017.
PCT/JP2017/037200, "English translation of International Search Report", dated Dec. 12, 2017.
PCT/JP2017/037178, "English translation of International Search Report", dated Dec. 26, 2017.
CN201780057377.2, "First Office Action" with Machine Translation, dated Jan. 26, 2021, 19 pages.

* cited by examiner

ENDOSCOPE CAP, ENDOSCOPE AND METHOD OF DETACHING ENDOSCOPE CAP

CROSS-REFERENCE TO RELATED APPLICATIONS

This application is the national phase under 35 U.S.C. § 371 of PCT International Application No. PCT/JP2017/037108 which has International filing date of Oct. 13, 2017 and designated the United States of America.

FIELD

The technology herein relates to an endoscope cap, an endoscope and a method of detaching an endoscope cap.

BACKGROUND

An endoscope having an elevator at the distal end of a channel passing through the inside of an insertion part has been used.

The elevator is used to bend a treatment tool or the like inserted into the channel and guide the tool to have a desired orientation.

An endoscope provided with a wall between an elevator and an elevating wire which moves the elevator is disclosed (Japanese Patent Application Laid-Open Publication No. 8-56900).

The endoscope disclosed in Japanese Patent Application Laid-Open Publication No. 8-56900 has a complicated structure around the elevator, which requires a lot of trouble in cleaning.

According to an aspect, an object is to provide an endoscope cap with an elevator which is easily attached to and detached from the distal end of the endoscope.

An endoscope cap attachable to and detachable from an endoscope including a lever pivotally provided at a distal end of an insertion part of the endoscope and a pivot part causing the lever to pivot, comprises: a bottomed cylindrical cover that has an opening end and is capable of attaching and detaching the opening end to and from the insertion part of the endoscope; a first engagement part located at an inner surface of the cylindrical part of the cover; and an elevator that has a lever connection part connected to the lever and that is pivotally fixed to the inner side of the cover.

According to an aspect, an endoscope cap or the like with an elevator which is easily attached to and detached from the distal end of the endoscope may be provided.

DETAILED DESCRIPTION OF NON-LIMITING EXAMPLE EMBODIMENTS

Embodiment 1

Figure 1:
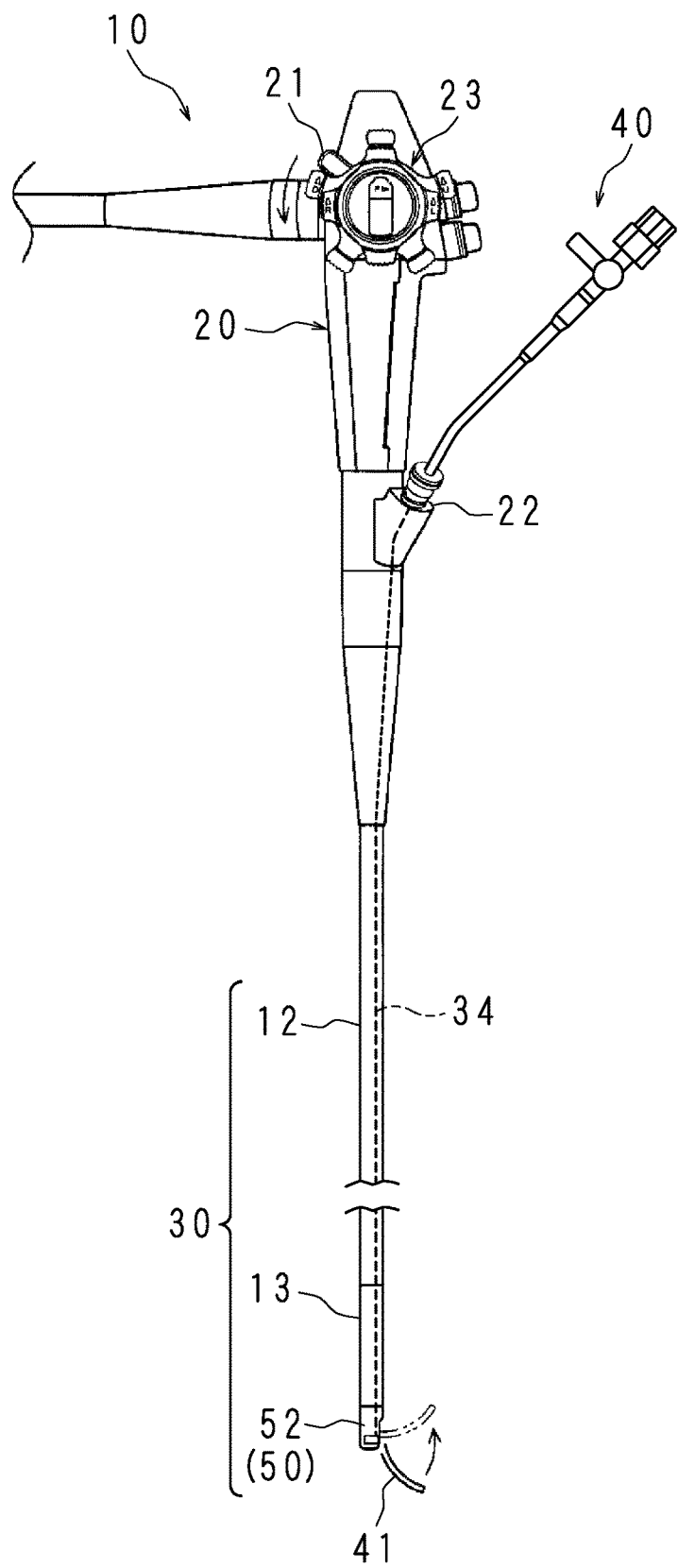
FIG. 1 illustrates an outer appearance of an endoscope.

FIG. 1 illustrates the outer appearance of an endoscope. An endoscope 10 according to the present embodiment is a flexible endoscope directed to an upper gastrointestinal tract. The endoscope 10 has an operation part 20 and an insertion part 30. The operation part 20 has an elevator operation lever 21, a channel inlet 22 and a bending knob 23. The operation part 20 is connected to a video processor, a light source device, a display device and so forth that are not illustrated.

The insertion part 30 is long, and has one end connected to the operation part 20. The insertion part 30 has, from the operation part 20 side, a flexible section 12, a bending section 13 and an endoscope cap 50. The flexible section 12 is flexible. The bending section 13 bends in response to the operation of the bending knob 23. The endoscope cap 50 covers a rigid distal end portion 31 (see FIG. 2) that is continuous from the bending section 13.

In the endoscope 10 according to the present embodiment, the endoscope cap 50 may be attached to or detached from the distal end portion 31. The endoscope cap 50 has a cover 52 which is an exterior member and an elevator 80 (see FIG. 2). The detailed structure of the endoscope cap 50 will be described later.

In the following description, the longitudinal direction of the insertion part 30 will be referred to as an insertion direction. Likewise, along the insertion direction, the side closer to the operation part 20 will be referred to as a proximal side, whereas the side farther from the operation part 20 will be referred to as a distal side.

Figure 2:
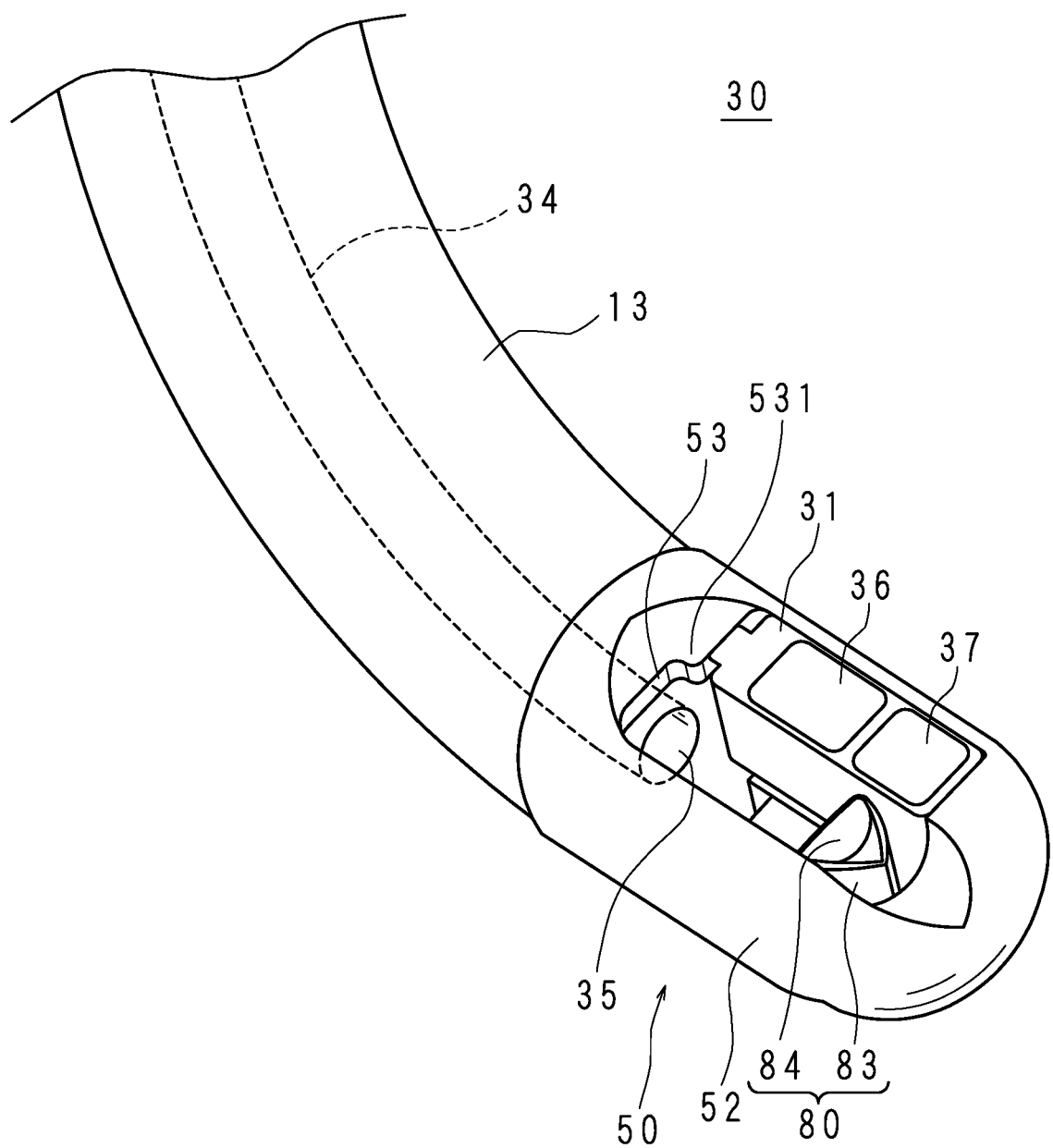
FIG. 2 is a perspective view of a distal end of an insertion part.
Figure 3:
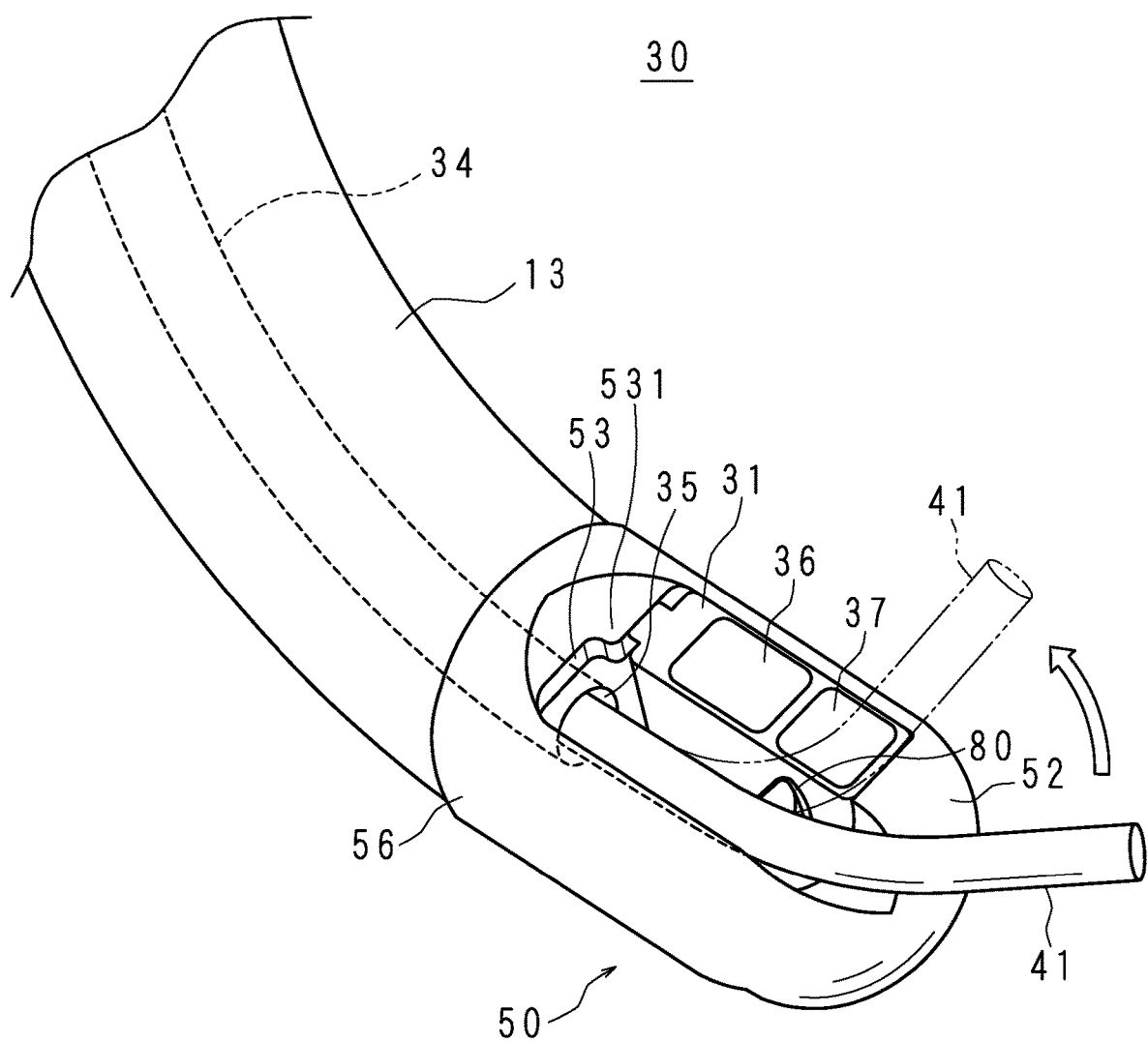
FIG. 3 illustrates a state where a treatment tool tip end protrudes from the distal end of the insertion part.

FIG. 2 is a perspective view of a distal end of the insertion part 30. FIG. 3 illustrates the state where a treatment tool tip end 41 protrudes from the distal end of the insertion part 30. The configuration of the endoscope 10 according to the present embodiment will be described with reference to FIGS. 1 to 3.

A distal end portion 31 located at the distal end of the bending section 13 has, on one side thereof, an observation window 36 and an illumination window 37 that are aligned along the insertion direction. The illumination window 37 is located more toward the distal side than the observation window 36. The distal end portion 31 has a channel outlet 35 at the proximal side on the other side thereof. An elevating part 83 is disposed at the distal side of the channel outlet 35. The cover 52 which covers the distal end portion 31 has a substantially rectangular window part 53 at a portion corresponding to the observation window 36, illumination window 37 and elevating part 83. The side of the window part 53 on the proximal side has a stepped shape with one step where the elevating part 83 side is located on the proximal side whereas the observation window 36 side is located on the distal side, and has a stopper 531 at the middle part.

The illumination window 37 directs the illumination light emitted from a light source device (not illustrated). Through the observation window 36, it is possible to optically observe the area irradiated with the illumination light. The endoscope 10 according to the present embodiment is of a so-called side view type, in which a viewing direction for optical observation is a direction intersecting the insertion direction. The endoscope 10 may also be of a forward oblique view type with a viewing direction somewhat inclined toward the distal side or a backward oblique view type with a viewing direction somewhat inclined toward the proximal side.

The channel inlet 22 and the channel outlet 35 are connected with each other by a channel 34 running through the inner side of the flexible section 12 and the bending section 13. The treatment tool 40 may be inserted through the channel inlet 22 from the treatment tool tip end 41, to protrude the treatment tool tip end 41 from the channel outlet 35.

As illustrated by the solid line in FIG. 3, the treatment tool tip end 41 protrudes while curving gently over the elevating part 83. If the elevator operation lever 21 is operated as illustrated by the arrow in FIG. 1, a lever 60 (see FIG. 8) moves as described later, and an elevator 80 also moves in conjunction with the lever 60. As the elevator 80 moves, the treatment tool tip end 41 located over the elevator 80 is bent toward the proximal side, i.e. the operation part 20 side, as indicated by the arrows and dashed-two dotted lines in FIGS. 1 and 3. The movement of the treatment tool tip end 41 is photographed by an image sensor (not illustrated) or the like through the observation window 36, and is displayed on a display device (not illustrated).

The treatment tool 40 is an instrument for treatment, for example, a high-frequency knife, forceps or contrast tube. The instrument to be inserted into the channel 34 is not limited to the instrument for treatment. For example, an instrument for observation such as an ultrasound probe or ultra-slim endoscope may also be inserted into the channel 34 and used. In the following description, the treatment tool 40 includes an instrument for observation.

The movement of the elevator 80 as described above may be expressed as "the elevator 80 is elevated" in the description below. The bending of the treatment tool tip end 41 by being pushed by the elevated elevator 80 may also be expressed as "the treatment tool 40 is elevated" in the description below. The operation of the elevator operation lever 21 may adjust the degree of elevation of the treatment tool 40.

Figure 4:
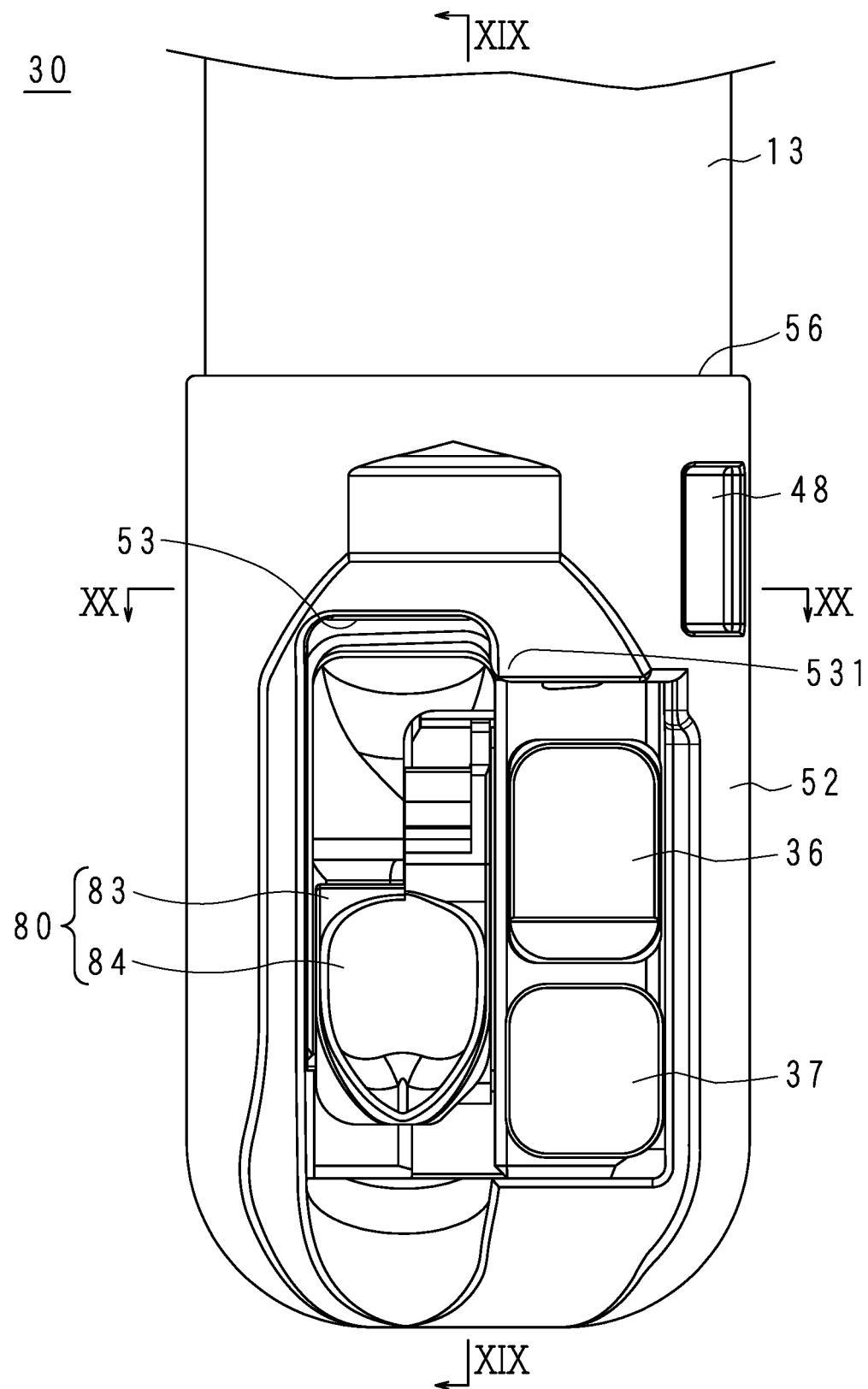
FIG. 4 is a front view of the distal end of the insertion part.

FIG. 4 is a front view of the distal end of the insertion part 30. The cover 52 has a rectangular concave part 48 in the vicinity of the opening end 56. Each side of the concave part 48 extends downward from the surface of the cover 52 so as to be substantially perpendicular thereto. The concave part 48 is a portion which is thinner than the other parts of the cover 52 in the circumferential direction, and is likely to flex when an external force is applied thereto by, for example, pressing the portion with a finger. The concave part 48 is an example of a flexible part according to the present embodiment.

Figure 5:
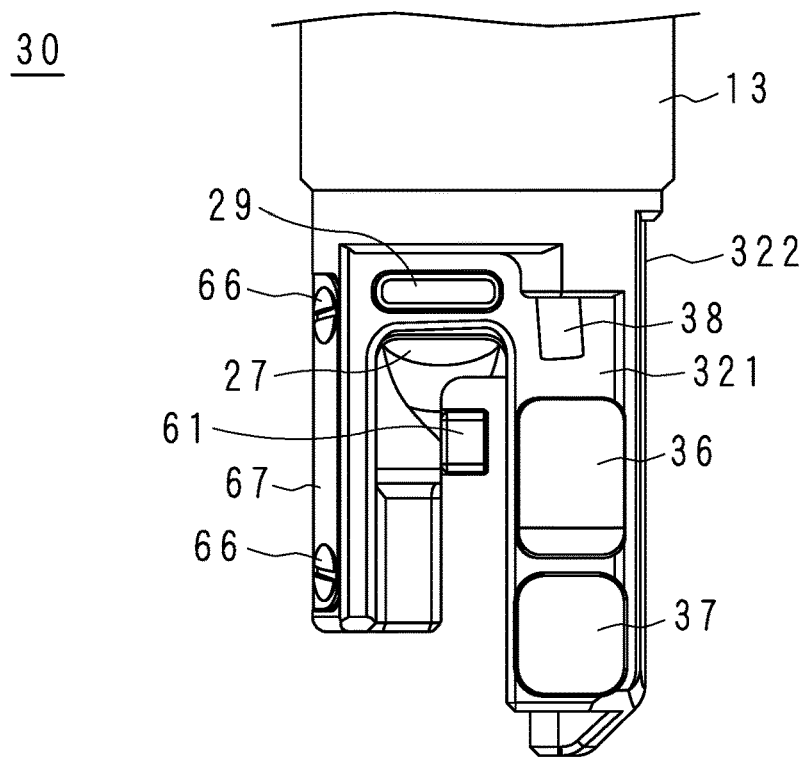
FIG. 5 is a front view illustrating the state where the endoscope cap is detached from the distal end of the insertion part.
Figure 5:
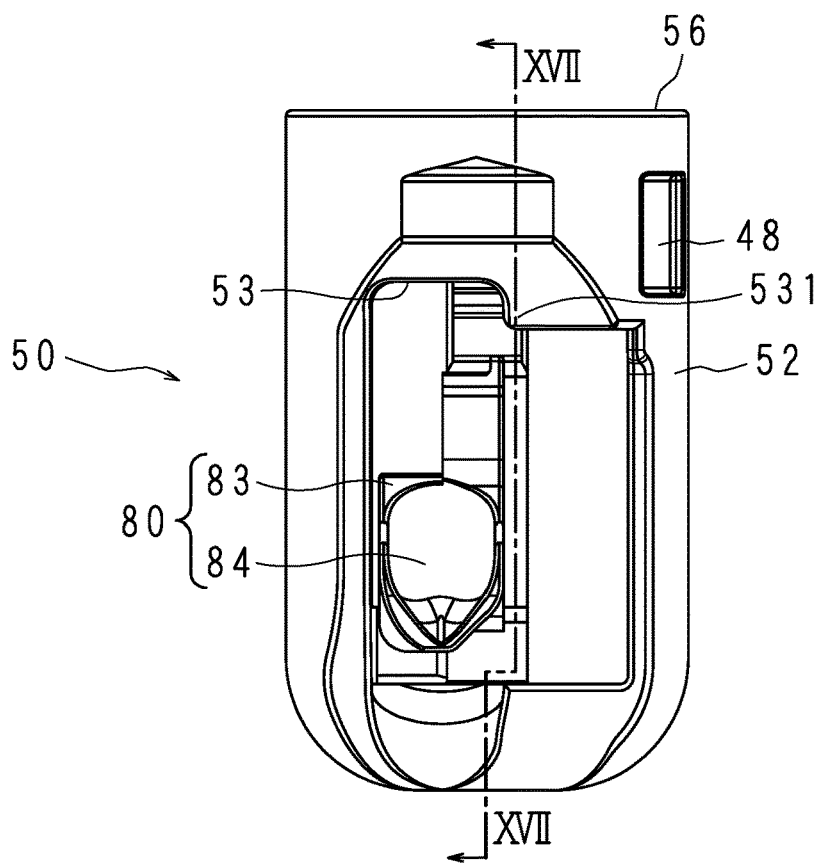
Figure 6:
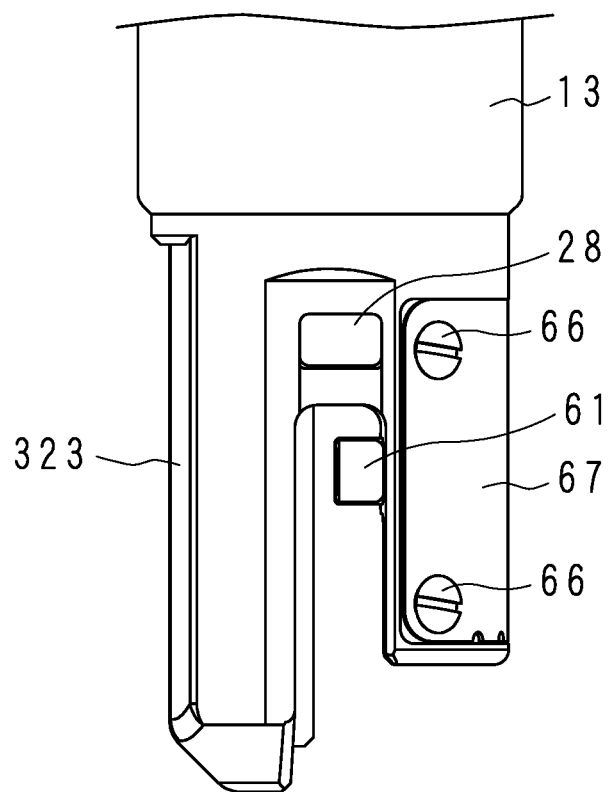
FIG. 6 is a back view illustrating the state where the endoscope cap is detached from the distal end of the insertion part.
Figure 6:
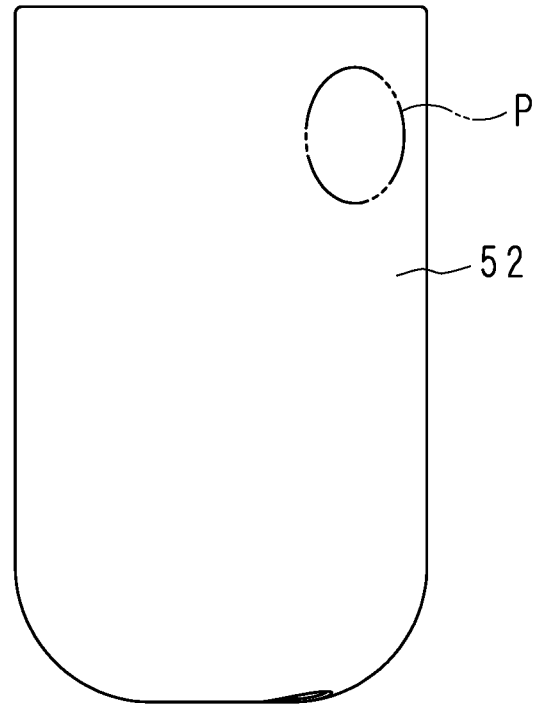

FIG. 5 is a front view illustrating the state where the endoscope cap 50 is detached from the distal end of the insertion part 30. FIG. 6 is a back view illustrating the state where the endoscope cap 50 is detached from the distal end of the insertion part 30. The user of the endoscope 10 holds the bending section 13 with one hand while pinching the cover 52 with two fingers of the other hand. Here, if one of the two fingers presses the concave part 48, the other finger naturally presses a region indicated by P in FIG. 6. After pressing and lightly deforming the cover 52 with two fingers, the user may pull the cover 52 toward the distal side to remove the endoscope cap 50 from the distal end of the insertion part 30 as described later.

Figure 7:
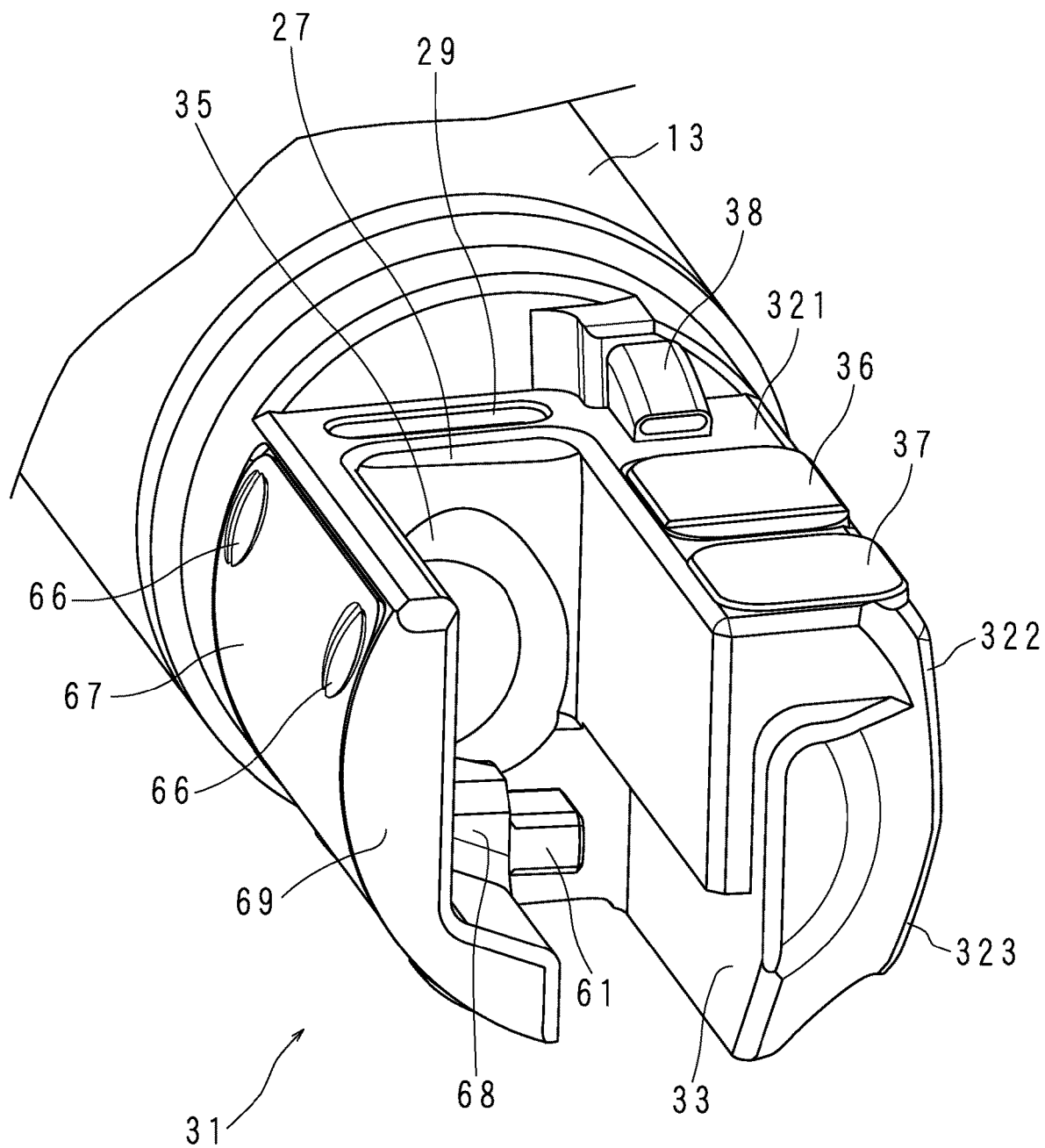
FIG. 7 is a perspective view of the distal end of the insertion part from which the endoscope cap is detached.

FIG. 7 is a perspective view of the distal end of the insertion part 30 from which the endoscope cap 50 is detached. The configuration of the distal end of the insertion part 30 will now be described with reference to FIGS. 5 to 7. The distal end portion 31 has a substantially columnar shape, and is divided into an optics housing 33 and a lever chamber 69 by a groove formed from the distal side to the proximal side at a position offset from the center. The channel outlet 35 is opened at the bottom of the groove. A bending part 27 is provided in the vicinity of the channel outlet 35. The shape of the bending part 27 will be described later.

The distal end portion 31 has a first planar part 321 formed by cutting a part of the circumferential surface to have a flat shape. The first planar part 321 is provided with a third engagement part 29 at a portion along the bottom of a groove which separates the optics housing 33 from the lever chamber 69. The third engagement part 29 is an oval recess. The distal end portion 31 has a fourth engagement part 28 (see FIG. 19) at the rear side of the third engagement part 29. The fourth engagement part 28 is a rectangular recess.

At the optics housing 33 side of the first planar part 321, the observation window 36 and the illumination window 37 are disposed. At the proximal side of the observation window 36, a nozzle 38 for injecting water and air to the observation window 36 to clean the observation window 36 is provided. Provided outside the optics housing 33 are a second planar part 322 and a third planar part 323 formed by cutting parts of the circumferential surface of the distal end portion 31 to have a flat shape. The second planar part 322 and the third planar part 323 are continuous, at an angle, with each other.

The lever chamber 69 is hollow and is covered by a lever chamber lid 67 having a rectangular thin plate-like shape which is along the outer peripheral surface of the distal end portion 31. The lever chamber lid 67 is fixed at four corners with lid screws 66. The lid screws are an example of a fixing member according to the present embodiment. The lever chamber 69 has a support wall 68 on the optics housing 33 side. The elevator connection part 61 protrudes from the support wall 68 toward the optics housing 33. The elevator connection part 61 is a shaft having a rectangular cross section. The elevator connection part 61 will be described later.

Figure 8:
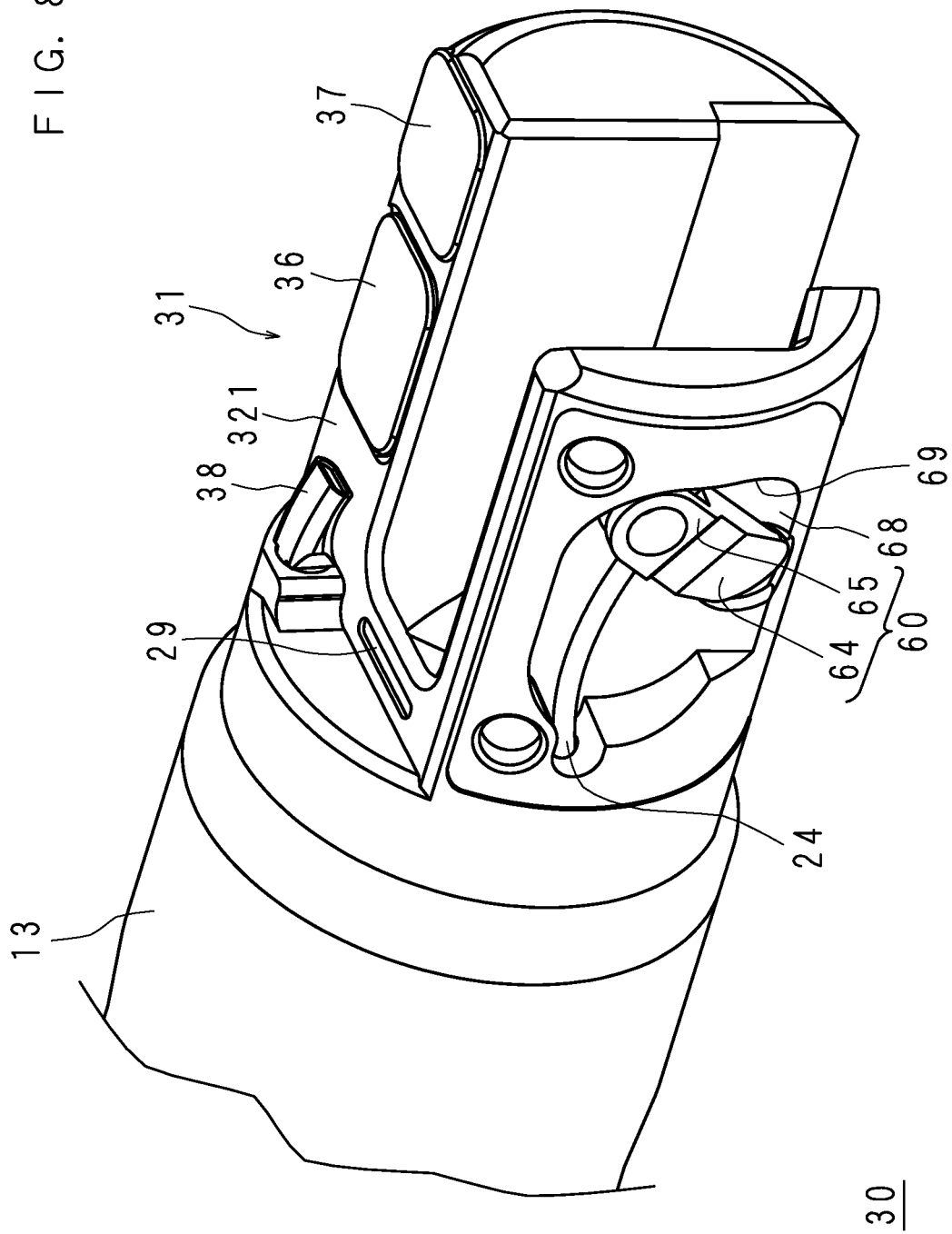
FIG. 8 is a perspective view of the distal end of the insertion part from which the endoscope cap and a lever chamber lid are detached.

FIG. 8 is a perspective view of the distal end of the insertion part 30 from which the endoscope cap 50 and the lever chamber lid 67 are detached. The lever 60 is located inside the lever chamber 69. The lever 60 has a wire fixing part 65 at one end thereof, while having a lever shaft 63 (see FIG. 19) and the elevator connection part 61 at the other end thereof, which will be described later. The lever 60 is pivotally supported to a hole opened at the support wall 68. It is noted that the pivot means rotary motion within a predetermined angle range.

The wire fixing part 65 is connected to an end of the elevating wire 24. The elevating wire 24 passes through the insertion part 30 and is connected to the elevator operation lever 21 (see FIG. 1). More specifically, the elevating wire 24 is inserted through a guide tube (not illustrated) having an inner diameter somewhat larger than the outer diameter of the elevating wire 24. The guide tube (not illustrated) penetrates through the insertion part 30 along the longitudinal direction. Thus, the distal end of the elevating wire 24 moves back and forth in cooperation with the operation of the elevator operation lever 21. The elevating wire 24 is an example of the rotation part according to the present embodiment. The elevating wire 24 is operated remotely by the elevator operation lever 21.

As the elevator operation lever 21 moves, the elevating wire 24 connected to the elevator operation lever 21 is pulled toward the proximal side. Being pulled by the elevating wire 24, the lever 60 pivots around the lever shaft 63.

Figure 9:
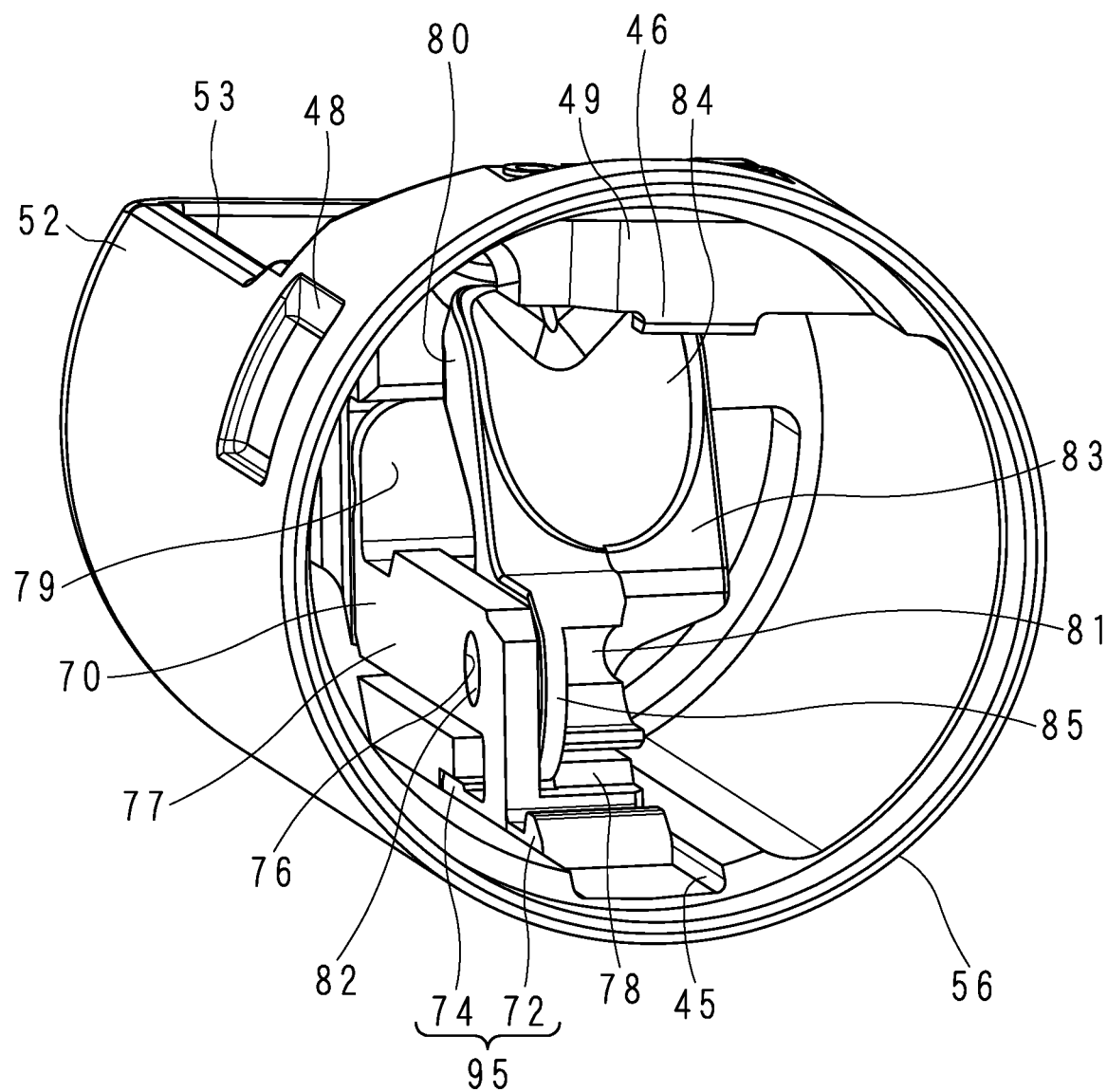
FIG. 9 is a perspective view of the endoscope cap when viewed from the attachment side to the endoscope.
Figure 10:
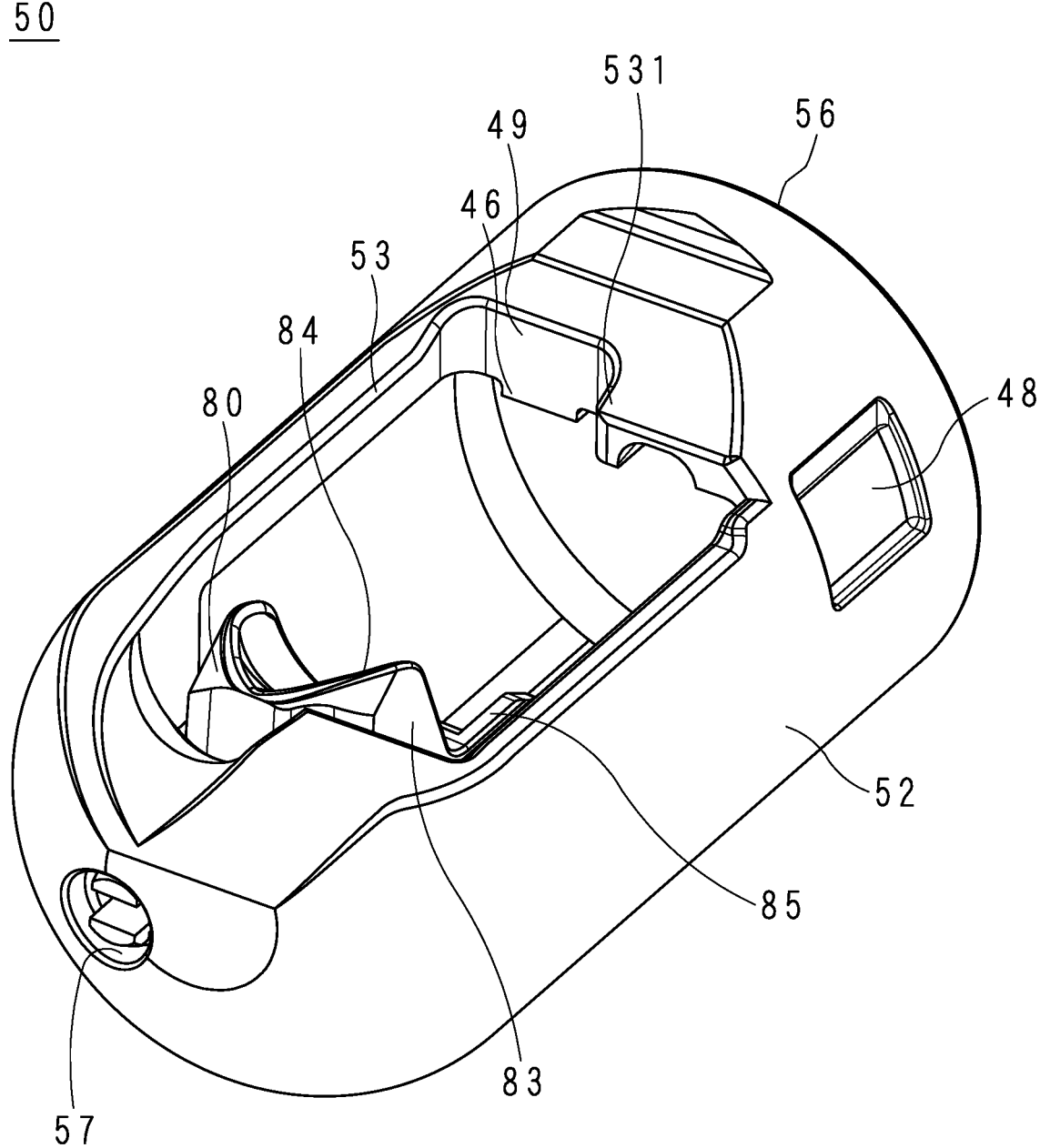
FIG. 10 is a perspective view of the endoscope cap when viewed from the bottom side of a cover.

FIG. 9 is a perspective view of the endoscope cap 50 when viewed from the attachment side to the endoscope 10. FIG. 10 is a perspective view of the endoscope cap 50 when viewed from the bottom side of the cover 52. As described earlier, the endoscope cap 50 has a cover 52 and an elevator 80. The cover 52 has a bottomed cylindrical shape having an opening end at one end thereof. In the description below, the opening at one end of the cover 52 is described as an opening end 56.

As described earlier, the cover 52 has a window part 53 at the cylindrical part. The window part 53 is opened at one portion of the peripheral surface of the cover 52 along substantially the entire length. The cover 52 has a pedestal groove 45 extending from the opening end 56 toward the bottom at an inner surface opposed to the window part 53. The elevator 80 is mounted to the inside of the cover 52 through the pedestal 70 fixed to the pedestal groove 45. The pedestal 70 will be described later.

The cover 52 has a plate-like protrusion 49 protruding inward along the edge on the opening end 56 side of the window part 53. A plate-like first engagement part 46 further protrudes from a part of the tip end of the protrusion 49. The protrusion 49 and the first engagement part 46 are made flush along the edge of the window part 53.

Figure 11:
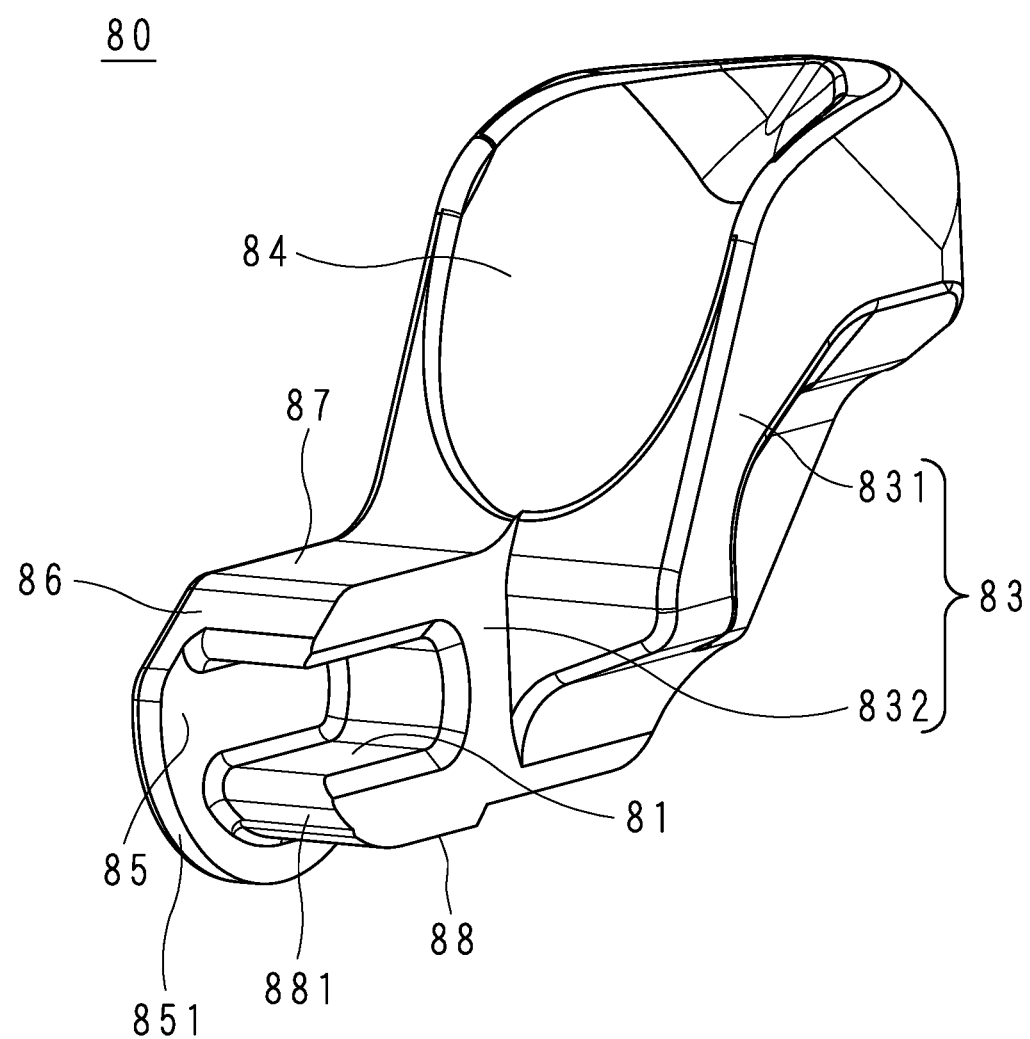
FIG. 11 is a perspective view of an elevator.
Figure 12:
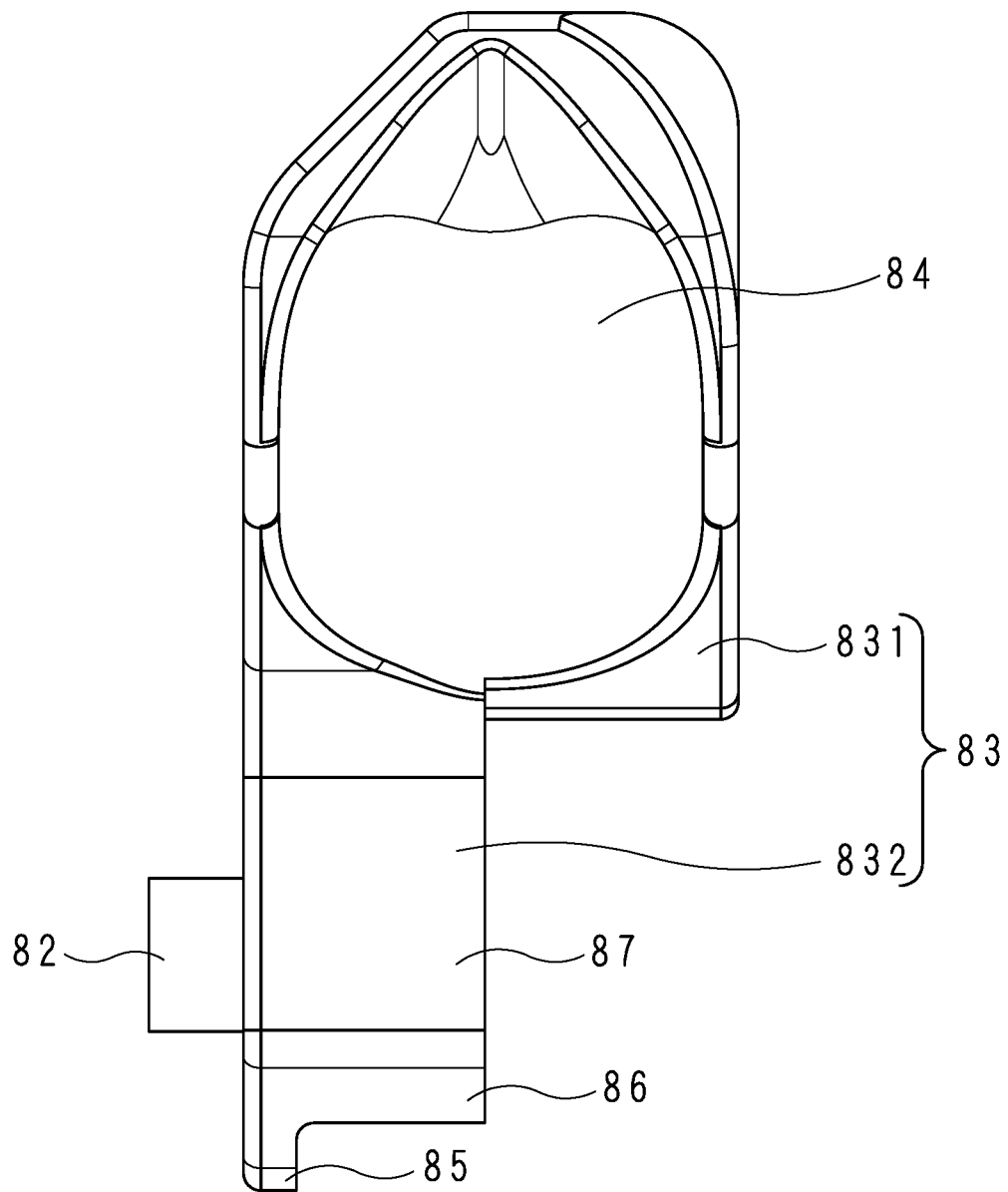
FIG. 12 is a front view of the elevator.
Figure 13:
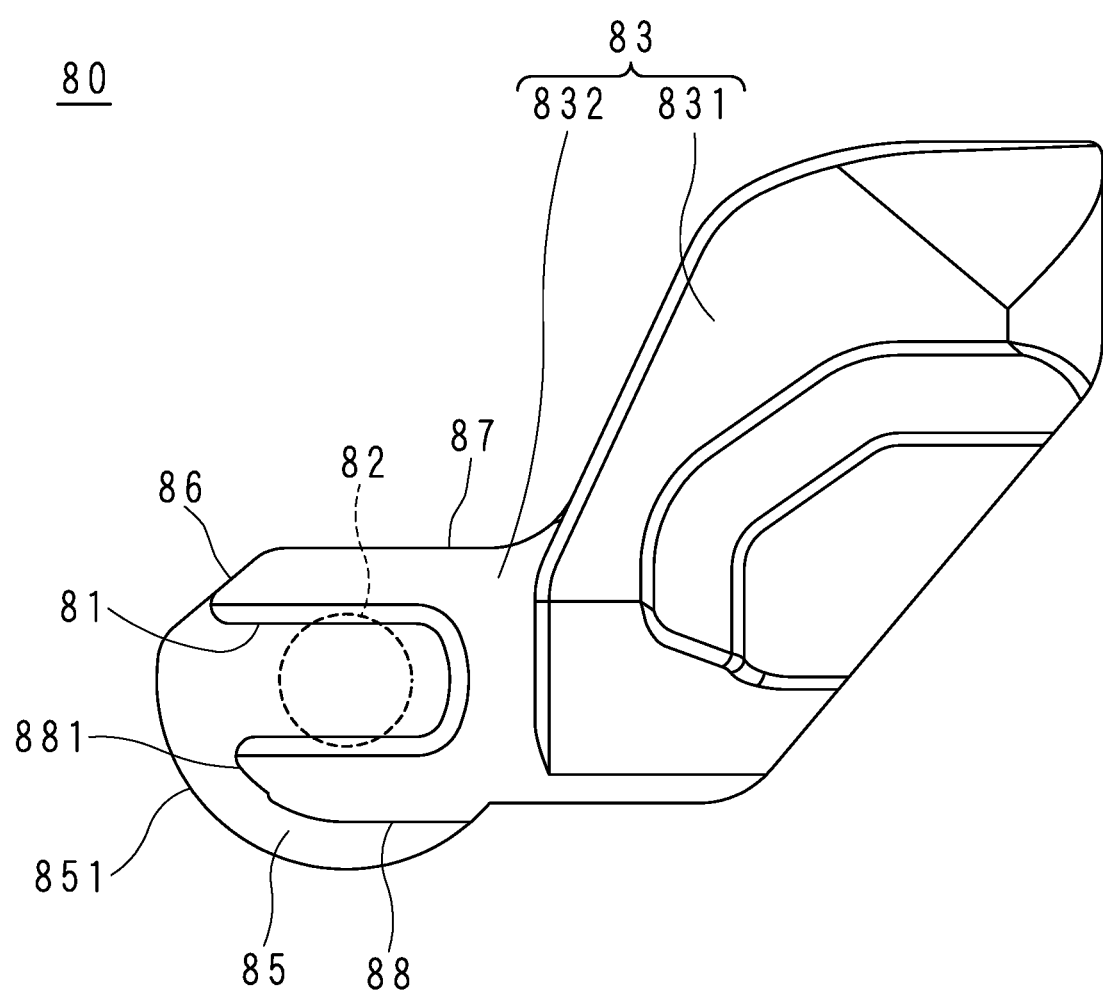
FIG. 13 is a side view of the elevator.

FIG. 11 is a perspective view of the elevator 80. FIG. 12 is a front view of the elevator 80. FIG. 13 is a side view of the elevator 80. The configuration of the elevator 80 will be described with reference to FIGS. 11 to 13.

The elevator 80 has a substantially L-shaped elevating part 83. The elevating part 83 has, at one surface thereof, a spoon-shaped first elevating part 831 having a recess 84, and a second elevating part 832 protruding from the edge of the first elevating part 831 on the same side as the surface of the first elevating part 831 that has the recess 84. The lever connection part 81 is located at an end of the second elevating part 832. The lever connection part 81 is a U-shaped groove opened toward an end of the second elevating part 832.

One side of the lever connection part 81 is covered with a plate-like flange 85. The elevator shaft 82 protrudes from a surface of the flange 85 on the opposite side. That is, the elevator shaft 82 protrudes from one surface of the flange 85, while the elevating part 83 protrudes from the other surface of the flange 85 in a direction intersecting the central axis of the elevator shaft 82. The lever connection part 81 is located at a base end side of the elevating part 83.

As indicated by the broken line in FIG. 13, the lever connection part 81 is so disposed as to have the central axis of the elevator shaft 82 therein. The flange 85 has a cylindrical surface 851 which is substantially coaxial with the elevator shaft 82.

The second elevating part 832 has a planar second flank 87 at a portion adjacent to the surface of the first elevating part 831 that has the recess 84. The second flank 87 is a flat surface parallel to the surface corresponding to two vertical lines of the U-shaped lever connection part 81.

The second elevating part 832 has a first flank 86 between the second flank 87 and the inlet of the lever connection part 81. The first flank 86 is a flat surface disposed more toward the central axis of the elevator shaft 82 than the extended surface of the cylindrical surface 851 located at the flange 85. The edge of the first flank 86 on the flange 85 side is contiguous to the cylindrical surface 851.

The second elevating part 832 has a stop surface 88 on the opposite side of the second flank 87 across the lever connection part 81. The stop surface 88 is a flat surface which is parallel to the second flank 87. The stop surface 88 is disposed more toward the central axis of the elevator shaft 82 than the extended surface of the cylindrical surface 851. The stop surface 88 is contiguous to the inlet of the lever connection part 81 through a substantially cylindrical pivot flank 881.

Figure 14:
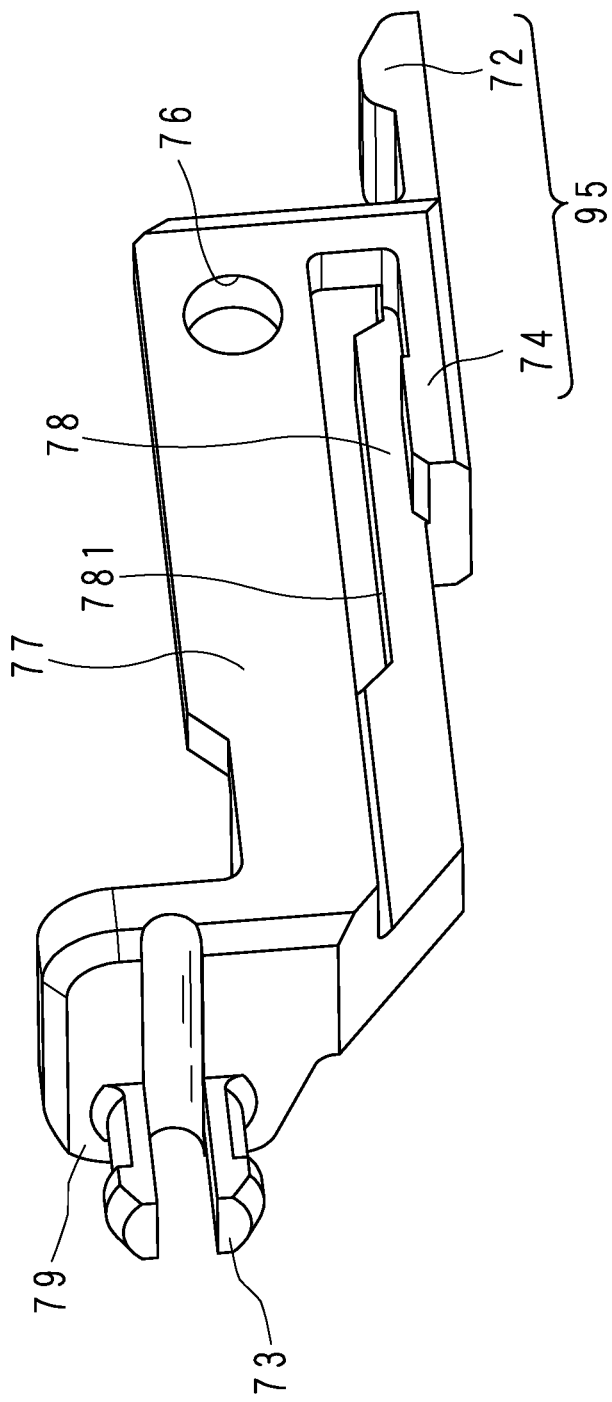
FIG. 14 is a perspective view of a pedestal.

FIG. 14 is a perspective view of the pedestal 70. The configuration of the pedestal 70 will be described with reference to FIG. 14.

The pedestal 70 has a rectangular plate-like foundation 95 and a substantially rectangular plate-like first wall 77 extending along the longitudinal direction of the foundation 95 from a support foot rising from the middle part in the longitudinal direction of the foundation 95.

Furthermore, from the foundation 95, a substantially rectangular plate-like second wall 78 rises in parallel to the first wall 77. The first wall 77 and the second wall 78 are separated from each other in the width direction of the foundation 95. The second wall 78 has a second wall end face 781 which is parallel to the foundation 95. The second wall end face 781 is located more toward the foundation 95 than the edge of the first wall 77.

To the end of the first wall 77, a rectangular plate-like third wall 79 which bridges the first wall 77 and the second wall 78 is connected. The third wall 79 is provided with a first fixing projection 73 on a surface opposite from the first wall 77. The first fixing projection 73 is a projection having an expanding slot. The first fixing projection 73 has, at an end thereof, a retainer with a diameter one size larger than that of the projection 73.

The foundation 95 has a thick part 74 at one end thereof in the longitudinal direction, and has a second engagement part 72 bulged in a substantially semicircular shape at the opposite end thereof. The thick part 74 is opposed to the first wall 77.

The first wall 77 has an elevator attachment hole 76 at the root. The elevator shaft 82 of the elevator 80 described with reference to FIGS. 11 to 13 is inserted into the elevator attachment hole 76, to combine the elevator 80 and the pedestal 70 together so as to be pivotable.

Figure 15:
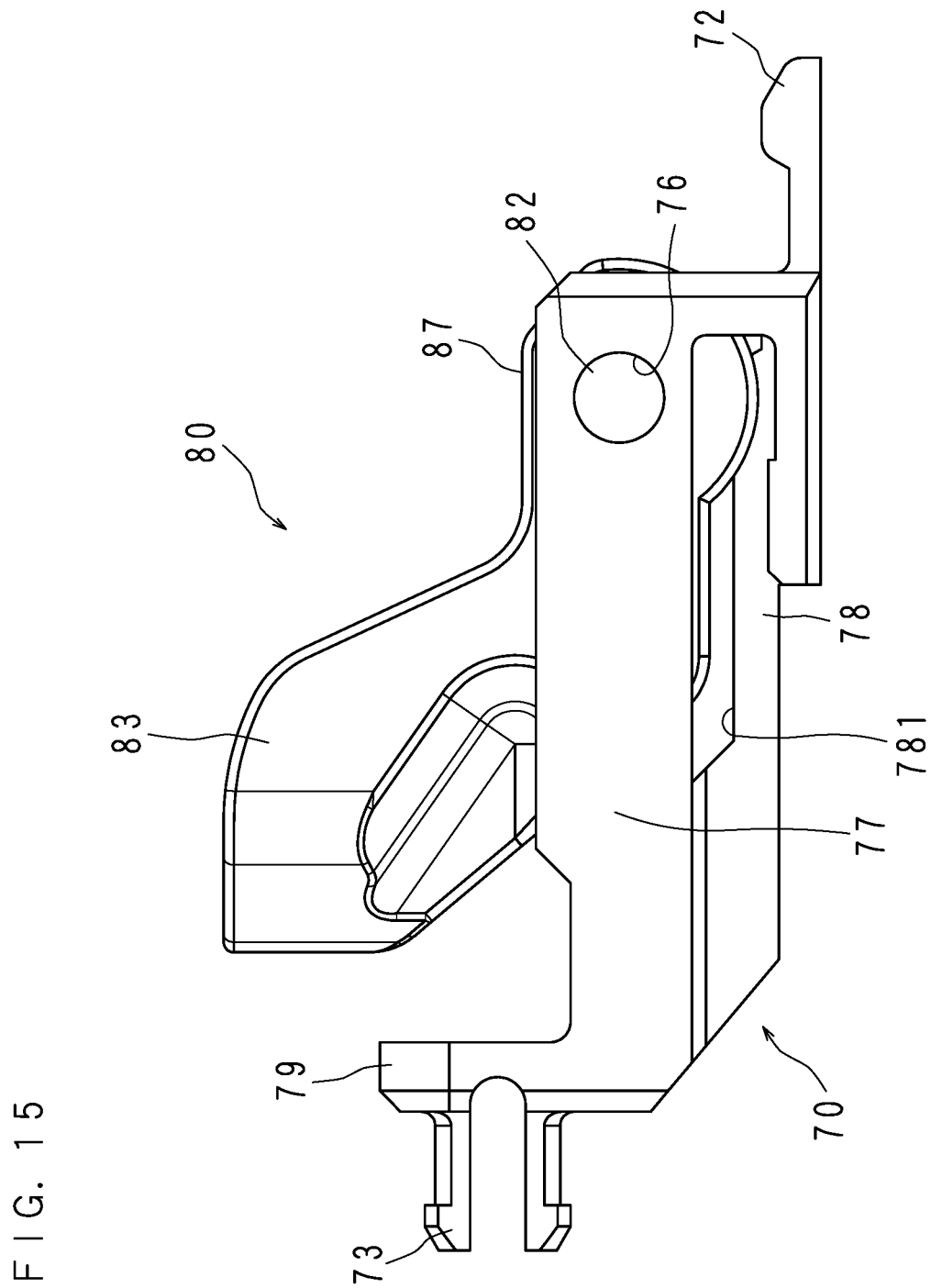
FIG. 15 is a front view of the elevator and the pedestal combined together.
Figure 16:
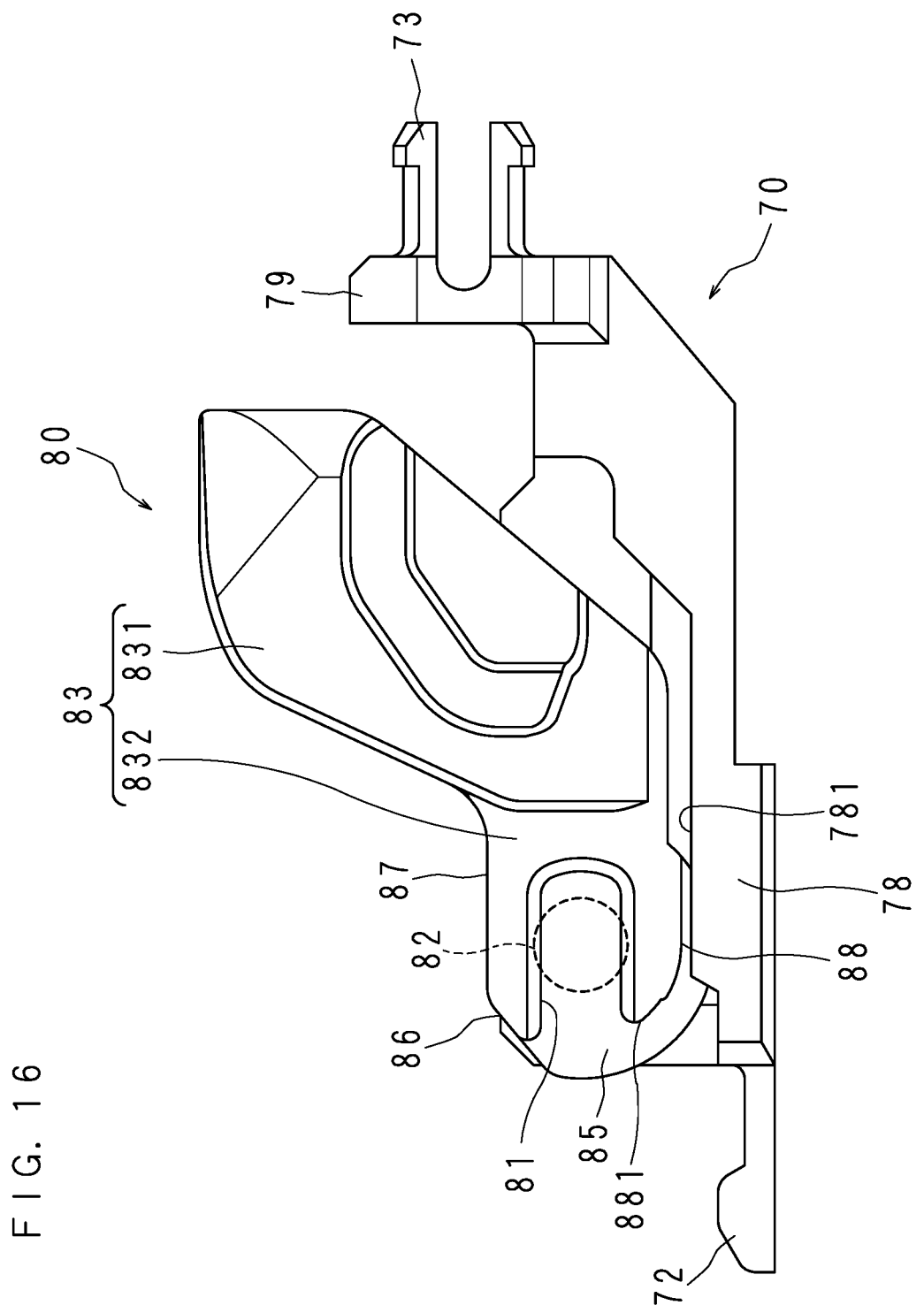
FIG. 16 is a back view of the elevator and the pedestal combined together.

FIG. 15 is a front view of the elevator 80 and the pedestal 70 combined together. FIG. 16 is a back view of the elevator 80 and the pedestal 70 combined together. The configuration of the elevator 80 and the pedestal 70 that are combined together will be described with reference to FIGS. 15 and 16.

As described earlier, the elevator shaft 82 is inserted into the elevator attachment hole 76. The elevator attachment hole 76 serves as a bearing, so that the elevator 80 may be pivotable about the elevator shaft 82. The flange 85 is held between the first wall 77 and the second wall 78. The flange 85 and the second wall 78 serve as a stopper, which prevents the elevator 80 from coming off the pedestal 70.

The stop surface 88 is opposed to the second wall end face 781. In the case where a force in the direction of clockwise rotation in FIG. 16 about the elevator shaft 82 is applied to the elevator 80, the stop surface 88 makes contact with the second wall 78 to prevent the elevator 80 from rotating. Meanwhile, since the opening end 56 side of the stop surface 88 is contiguous to the inlet of the lever connection part 81 through the substantially cylindrical pivot flank 881, the elevator 80 is able to rotate in the anticlockwise direction in FIG. 16 about the elevator shaft 82.

Description continues with reference to FIG. 9 again. The pedestal 70 is inserted into the cover 52 from the first fixing projection 73 side while the elevator 80 is pivotally attached to the elevator attachment hole 76. The foundation 95 of the pedestal 70 is fixed to the pedestal groove 45.

Figure 17:
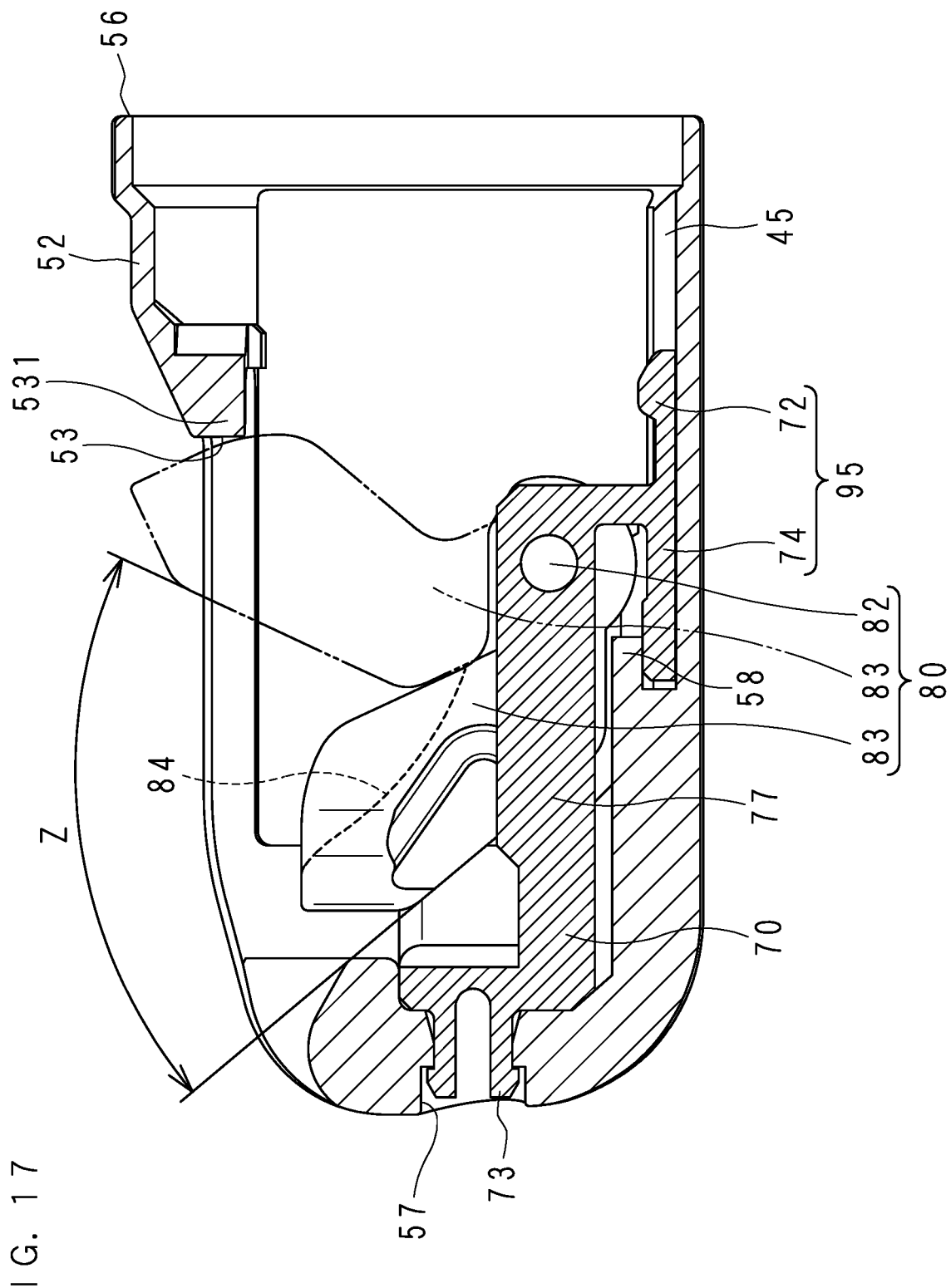
FIG. 17 is a section view of an endoscope cap taken along the line XVII-XVII in FIG. 5.

FIG. 17 is a section view of an endoscope cap 50 taken along the line XVII-XVII in FIG. 5. The XV-XV section is a cross section of the first wall 77 cut in the thickness direction along the longitudinal direction of the insertion part 30. The configuration of the endoscope cap 50 will be described with reference to FIGS. 9 to 17.

As illustrated in FIG. 17, the cover 52 has a pedestal fixing hole 57 and a second fixing projection 58. The pedestal fixing hole 57 is a through hole opened at the bottom of the cover 52. The second fixing projection 58 is a projection which projects from an end of the pedestal groove 45 toward the opening end 56 side.

Since the first fixing projection 73 and the thick part 74 described with reference to FIG. 14 are engaged with the pedestal fixing hole 57 and the second fixing projection 58, respectively, the elevator 80 and the pedestal 70 may be fixed to each other inside the cover 52. The recess 84 is opposed to the window part 53.

As indicated by a dashed-two dotted line in FIG. 17, the elevator 80 may pivot about the elevator shaft 82 to a position where the edge of the elevating part 83 makes contact with the stopper 531. In the description below, the pivotable angle of the elevator 80 will be described as an angle Z.

Figure 18:
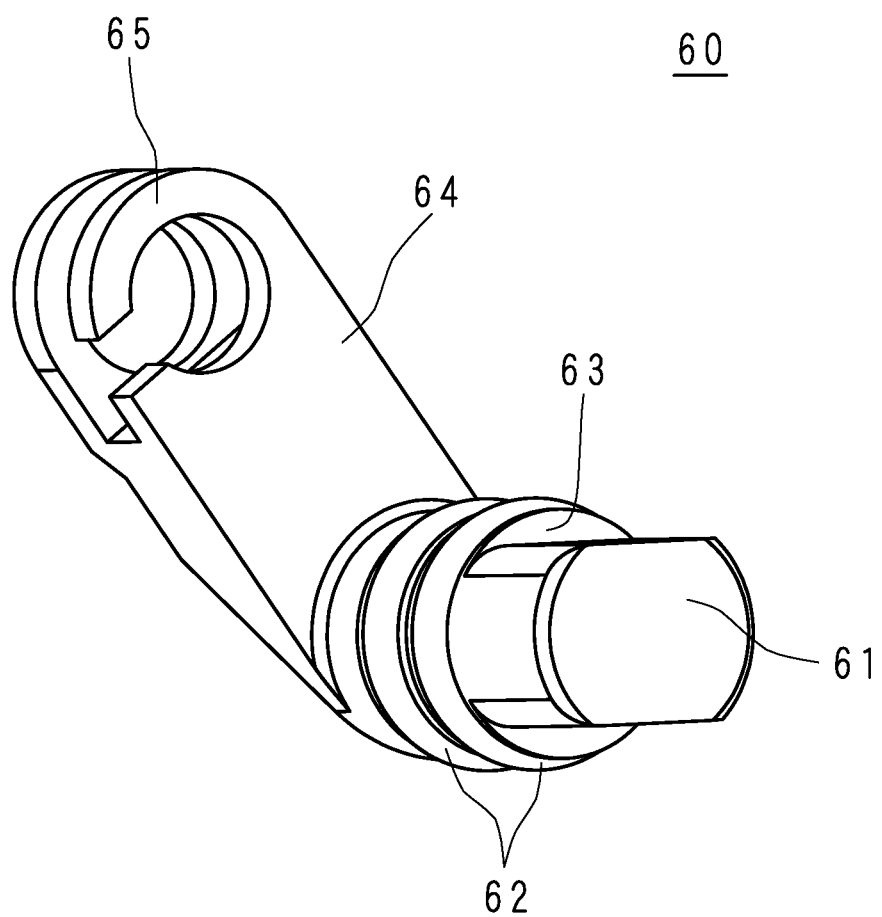
FIG. 18 is a perspective view of a lever.

FIG. 18 is a perspective view of the lever 60. The lever 60 has a lever shaft 63 at one end thereof and a wire fixing part 65 at the other end thereof. The wire fixing part 65 is provided with an expanding slot. The elevator connection part 61 which is a shaft with a rectangular cross section protrudes from one end face of the lever shaft 63 in the same direction as the central axis of the lever shaft 63. In the description below, a plate-like portion which connects the lever shaft 63 and the wire fixing part 65 will be described as a pivot connection part 64. The pivot connection part 64 protrudes from the other end of the lever shaft 63 that is opposite from the elevator connection part 61 in a direction intersecting the central axis of the lever shaft 63. As illustrated in FIG. 8, the pivot connection part 64 pivots in the lever chamber 69. That is, the lever 60 is provided at the distal end of the insertion part 30 of the endoscope 10 so as to be pivotable about the lever shaft 63.

Two O-rings 62 are fixed to the lever shaft 63. Description continues with reference to FIG. 7 again. In the lever 60, the lever shaft 63 is inserted into a hole opened at the support wall 68 from the lever chamber 69 side, and is so supported as to be pivotable while the elevator connection part 61 faces the optics housing 33. The O-rings 62 and the lever chamber lid 67 seal the hollow lever chamber 69 in a water-tight manner.

Figure 19:
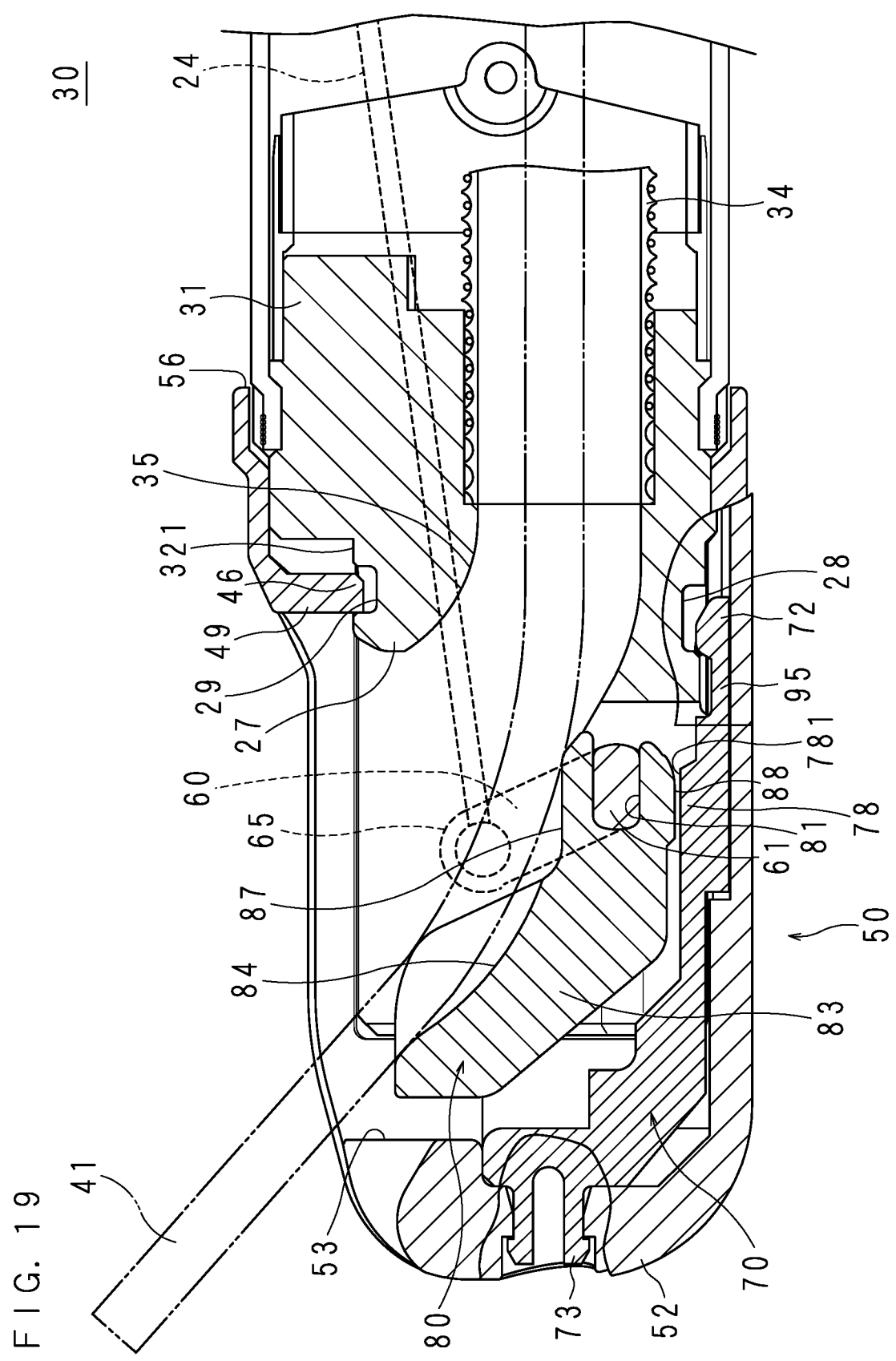
FIG. 19 is a section view of the insertion part taken along the line XIX-XIX in FIG. 4.
Figure 20:
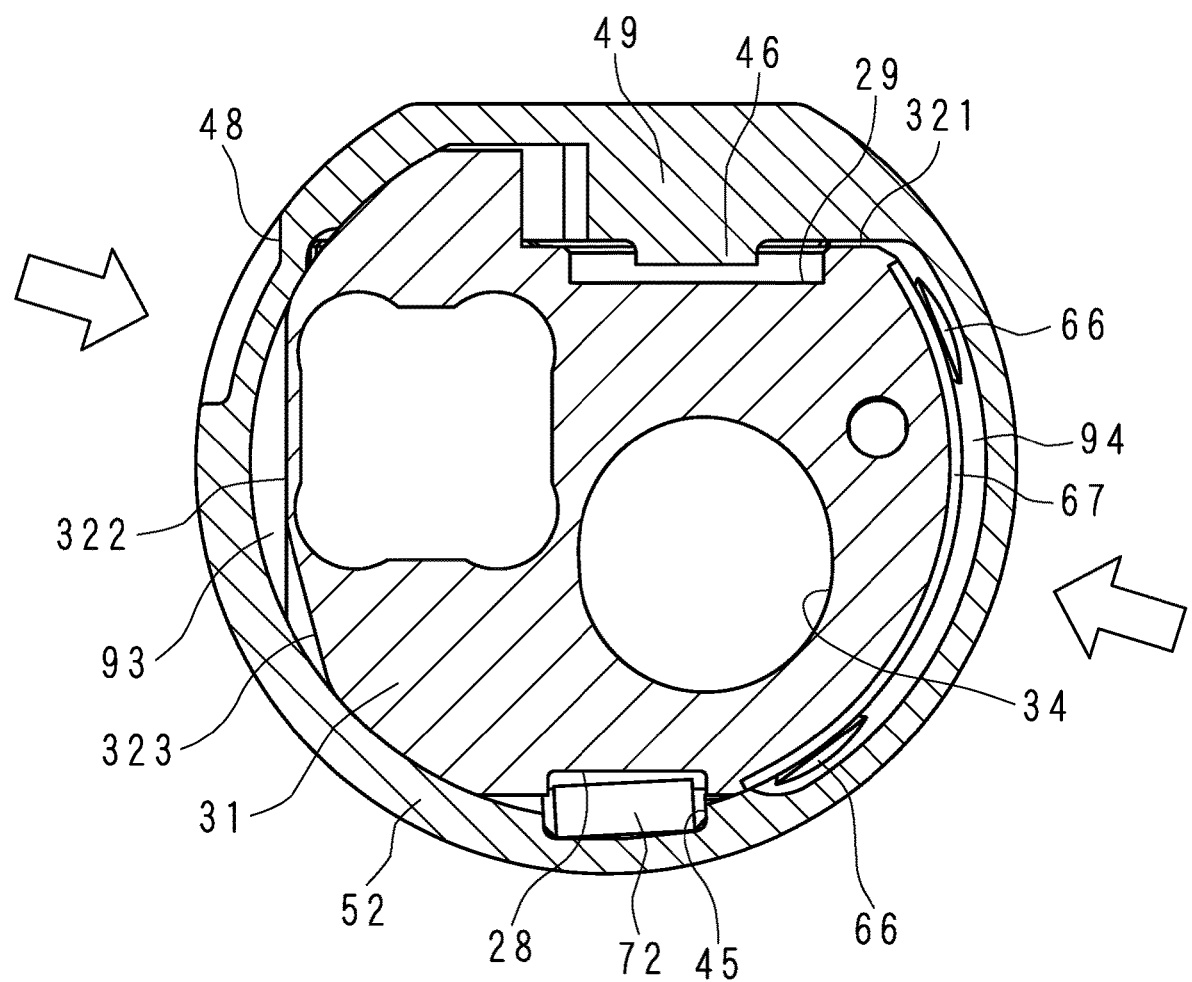
FIG. 20 is a section view of the insertion part taken along the line XX-XX in FIG. 4.

FIG. 19 is a section view of the insertion part 30 taken along the line XIX-XIX in FIG. 4. The XIX-XIX section is a cross section which passes the elevator connection part 61 along the longitudinal direction of the insertion part 30. FIG. 20 is a section view of the insertion part 30 taken along the line XX-XX in FIG. 4. The XX-XX section is a cross section which passes the edge of the fourth engagement part 28 on the proximal side and the third engagement part 29, and is perpendicular to the insertion part 30 in the longitudinal direction. The configuration where the endoscope cap 50 is fixed to the distal end of the insertion part 30 will be described with reference to FIGS. 19 and 20.

The endoscope cap 50 has the opening end 56 facing the insertion part 30. The first engagement part 46 at the inner surface of the endoscope cap 50 is engaged with the third engagement part 29 of the distal end portion 31. Likewise, the second engagement part 72 at the inner surface of the endoscope cap 50 is engaged with the fourth engagement part 28 of the distal end portion 31. The endoscope cap 50 is engaged with the distal end portion 31 at two opposed positions at the inner surface, so as to be fixed to the distal end portion 31.

As illustrated in FIG. 19, the first engagement part 46 is disposed more toward the opening end 56 side than the second engagement part 72. Furthermore, the first engagement part 46 and the third engagement part 29 are engaged by their flat surfaces abutting against each other, while the second engagement part 72 is engaged with the fourth engagement part 28 at its rounded surface. Thus, the first engagement part 46 is more securely engaged with the distal end portion 31 compared to the second engagement part 72.

The elevator connection part 61 which is a shaft having a rectangular cross section is inserted into the lever connection part 81 of a U-shaped groove. Thus, the lever 60 and the elevator 80 are engaged with each other. As described above, when the endoscope cap 50 is mounted to the distal end portion 31 of the endoscope 10, the elevator 80 is connected to the lever 60. Connection here means the state where the elevator 80 and the lever 60 pivot together if the lever 60 pivots.

As illustrated in FIG. 20, the inner surface of the cylindrical part of the cover 52 is opposed to the second planar part 322 and the third planar part 323 with a space in between, to form a first cavity 93. The concave part 48 is located at a position corresponding to the first cavity 93. At the opposite side of the concave part 48, the cover 52 is made thinner by making a dent at the inner surface of the cylindrical part. The inner surface of the thin part of the cover 52 and the lever chamber lid 67 are opposed to each other with a space in between, to form a second cavity 94.

The heads of lid screws 66 are disposed in the second cavity 94. That is, the second cavity 94 is a space that accommodates the head of each lid screw 66 which is a fixing member for fixing the lever chamber lid 67.

As indicated by the outlined arrow in FIG. 20, the user presses two portions, i.e. the concave part 48 and the part opposite thereto, with fingers. Since the first cavity 93 and the second cavity 94 are present at the rear sides of the pressed portions, the cover 52 is deformed into a substantially elliptical shape with its short axis corresponding to the pressing direction and its long axis corresponding to the direction orthogonal to the pressing direction.

The first engagement part 46 and the second engagement part 72 described earlier are located near a portion corresponding to the long axis of the deformed cover 52. By the endoscope cap 50 being deformed, the first engagement part 46 and the second engagement part 72 move outward, respectively, to release the engagement between the third engagement part 29 and the fourth engagement part 28. As described earlier, the concave part 48 is thinner than the other parts of the cover 52 in the circumferential direction, and is a flexible part which is easily flexed by, for example, being pressed with a finger. This allows the user to easily deform the endoscope cap 50.

When the user pulls the endoscope cap 50 to the distal side while pressing it, the engagement between the lever connection part 81 and the elevator connection part 61 is released so that the endoscope cap 50 may be detached from the distal end of the insertion part 30. As illustrated in FIG. 4, the concave part 48 has a side orthogonal to the insertion direction. This allows the user to hook his/her finger on the edge of the concave part 48, which facilitates the removal of the endoscope cap 50.

It is noted that the user is able to attach the endoscope cap 50 to the insertion part 30 by pushing the endoscope cap 50 into the distal end of the insertion part 30 after confirming that the lever connection part 81 and the elevator connection part 61 are properly oriented. As illustrated in FIG. 19, the first engagement part 46 is chamfered at the opening end 56 side, which facilitates the attachment because the first engagement part 46 is not easily caught at the distal end portion 31.

As illustrated in FIG. 19, a tubular channel 34 is connected to the channel outlet 35 located at the distal end portion 31. The channel outlet 35 expands toward the window part 53 in a trumpet shape. A bending part 27 which gently protrudes toward the distal side is provided in the vicinity of the third engagement part 29 of the channel outlet 35.

Figure 21:
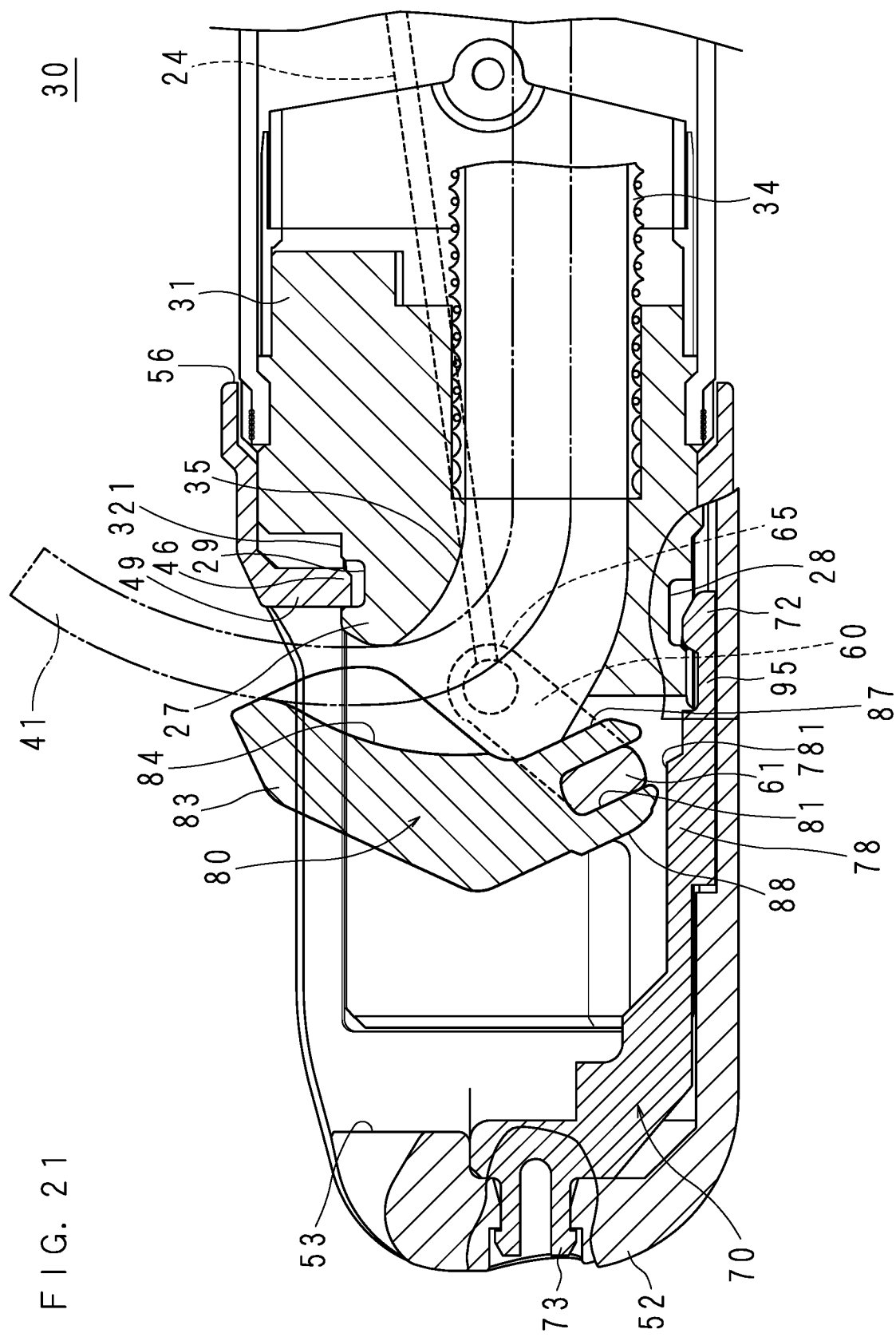
FIG. 21 is a section view of the insertion part in which an elevator is elevated.

FIG. 21 is a section view of the insertion part 30 in which the elevator 80 is elevated. FIG. 21 shows the same cross section as FIG. 19. The configuration of the elevator 80 being elevated will be described with reference to FIGS. 7, 8, 18, 19 and 20.

The lever shaft 63 is inserted into the through hole opened at the support wall 68 from the lever chamber 69 side, and the elevator connection part 61 protrudes from the opposite side of the support wall 68 as illustrated in FIG. 7. As described earlier, the lever chamber 69 is sealed to be water tight by the O-rings 62 and the lever chamber lid 67 (see FIG. 5). Therefore, the inside of the lever chamber 69 as well as the path of the elevating wire 24 may be prevented from body fluid or the like being adhered during use of the endoscope 10.

In the state illustrated in FIG. 19, the elevator 80 is accommodated inside the cover 52. The recess 84 is located at a position that allows the treatment tool tip end 41 protruding from the channel outlet 35 to bend gently upward in FIG. 19.

As described earlier, by the user operating the elevator operation lever 21, the lever 60 pivots about the lever shaft 63. The elevator connection part 61 pivots integrally with the lever shaft 63. Since the elevator connection part 61 is connected to the lever connection part 81, the elevator 80 also pivots to rise together with the lever 60. As a result, the distance between the elevator 80 and the window part 53 changes.

FIG. 21 illustrates the state where the elevator 80 is pivoted. Being pushed by the elevator 80, the treatment tool tip end 41 protruding from the channel outlet 35 is elevated. From the state of being pressed against the tip end of the bending part 27, the treatment tool tip end 41 is further pressed to the proximal side by the recess 84. This allows the treatment tool tip end 41 to bend at an angle larger than the pivotable angle Z of the elevator 80 as described with reference to FIG. 17.

A method of using the endoscope 10 according to the present embodiment will now be summarized. The endoscope 10 is stored in a state where the endoscope cap 50 is removed and is subjected to cleaning or the like. The endoscope cap 50 is enclosed in a sterile package one by one and, for example, ten such packages are put into a paper box which is then sterilized with electron beam. The number of the endoscope caps 50 to be put into a paper box may preferably be a minimum sales unit, i.e. a minimum sales unit to be sold to a user at a time. The user takes out the endoscope cap 50 from the sterile package and attaches the cap 50 to the distal end portion 31 of the endoscope 10.

The user inserts the insertion part 30 through the mouth of a subject for examination. While viewing a video image photographed via the observation window 36, the user guides the distal end of the insertion part 30 to a target site. The user inserts the treatment tool 40 or the like according to a purpose through the channel inlet 22. After confirming that the treatment tool tip end 41 protrudes from the distal end of the insertion part 30 and is located near the target site, the user operates the elevator operation lever 21 to guide the treatment tool tip end 41 to the target site. The user performs a necessary treatment or the like and then pulls out the treatment tool 40 from the channel 34. The user pulls out the endoscope 10 from the subject, and terminates the examination or treatment.

The cover 52 may easily be detached by being pulled to the distal side while being pressed with two fingers as described earlier. The endoscope cap 50 according to the present embodiment is so-called single use, and is discarded after one use.

In the case of observation and treatment using the endoscope 10 in a normal way, it is unlikely that an external force that is strong enough to deform the cover 52 is applied to two portions of the cover 52 at the same time.

The user performs a process such as cleaning on the endoscope 10 after the endoscope cap 50 is removed, to prepare for the next use. As illustrated in FIG. 7, the endoscope 10 after the endoscope cap 50 is removed has no elevator 80. The elevator connection part 61 used when the elevator 80 is fixed is exposed at the distal end portion 31, as illustrated in FIG. 7.

Accordingly, the endoscope 10 according to the present embodiment requires no special cleaning work for cleaning the complicated structure around the elevator 80 and the elevating wire 24. It is thus possible to provide the endoscope 10 with the elevator that has short process time between cases and that may efficiently be operated.

The stop surface 88 may not necessarily be parallel to the surface corresponding to two U-shaped vertical lines of the lever connection part 81. For example, in the case where the stop surface 88 is inclined toward the lower left in FIG. 19, the elevator 80 is able to rotate in the anti-clockwise direction from the state illustrated in FIG. 19. This can provide the endoscope 10 into which the treatment tool 40 may be inserted without greatly bending the treatment tool tip end 41.

In the case of elevating a highly rigid treatment tool 40, the elevating part 83 is pushed back by the force of the treatment tool 40 recovering to a straight state. Here, a twisting force in the anticlockwise direction in FIG. 21 about the second engagement part 72 is applied to the endoscope cap 50.

As described earlier, the first engagement part 46 is located closer to the opening end 56 compared to the second engagement part 72 and is more firmly engaged with the distal end portion 31 compared to the second engagement part 72, so that the endoscope cap 50 is unlikely to come off the insertion part 30. It is further possible to prevent the endoscope cap 50 from coming off the insertion part 30 by making the amount of protrusion of the first engagement part 46 larger than that of the second engagement part 72.

The endoscope 10 according to the present embodiment is provided with the elevator 80 and is of the side view type, which makes it suitable for diagnosis and treatment of duodenum and pancreaticobiliary duct areas. In particular, for the case of performing procedures such as endoscopic retrograde cholangio pancreatography (ERCP), endoscopic sphincterotomy (EST), endoscopic biliary drainage (EBD) and so forth, the endoscope 10 according the present embodiment is suitable. This is because, in these procedures, treatment or the like is performed by guiding the treatment tool 40 into the duodenum papilla on the duodenal wall as well as the pancreas duct, common bile duct and the like that are opened at the duodenum papilla.

The endoscope 10 of the side view type may also be referred to as a side view endoscope. Likewise, the endoscope 10 suitable for diagnosis or the like of the duodenum and pancreaticobiliary duct areas may also referred to as a duodenoscope.

According to the present embodiment, since the pedestal 70 and the cover 52 are separate members, their respective shapes are simple. It is thus possible to manufacture the components at lower cost by means of, for example, injection molding.

For the pivot part, an extendable shape memory alloy (SMA) actuator may also be employed instead of the elevating wire 24. In such a case, one end of the SMA actuator is fixed to the wire fixing part 65 whereas the other end thereof is fixed to the distal end portion 31. A heater is placed around the SMA actuator. The heater is configured to operate in conjunction with the movement of the elevator operation lever 21.

As the heater operates and the SMA actuator contracts, the lever 60 and the elevator 80 pivot. For the pivot part, any other linear actuator may also be employed.

A pivoting actuator such as a small motor may also be employed for the pivot part. The small motor is disposed in the lever chamber 69, and the motor shaft and the lever shaft 63 may be connected with each other to allow the lever 60 to pivot.

In the case where an actuator is employed for the pivot part, the elevator 80 may be operated by a means not using a hand of the user, such as voice control, for example.

The endoscope cap 50 may also be provided in the state where the elevator 80 and the cover 52 or the pedestal 70 are temporarily fixed to each other by an adhesive material or the like while the lever connection part 81 faces the opening end 56. Accordingly, the endoscope cap 50 which is used in a simple manner may be provided while eliminating the trouble of confirming the orientation of the elevator 80 before the endoscope cap 50 is attached to the insertion part 30.

It is also possible for the user to select and use an endoscope cap 50 with a specification according to a procedure from multiple types of endoscope caps 50 with different specifications. For example, an endoscope cap 50 provided with a stopper that restricts the pivotal range of the elevator 80 to be narrow may also be provided. In the case of using a combination of expensive and precise instruments such as an ultrasound probe or ultra-slim endoscope, for example, the narrowing of the pivotal range may prevent such instruments from being damaged by excessive bending.

In the case where the recess 84 has a shape contoured to the profile of the treatment tool tip end 41, the treatment tool 40 is unlikely to sway to the left and right at elevation, and thus tends to be easily operated. Multiple types of endoscope caps 50 having elevators 80 with recesses 84 of different shapes may be provided. For example, an endoscope cap 50 with a recess 84 having a shape that can easily hold a thin treatment tool 40 may be used to facilitate precise operation of the thin treatment tool 40 such as a guide wire.

Accordingly, the endoscope 10 for which the user may select and use the endoscope cap 50 suitable for a purpose may be provided.

The endoscope 10 may be a so-called ultrasound endoscope provided with an ultrasound transducer at the distal end. Here, the endoscope cap 50 may preferably have a hole at the bottom through which the ultrasound transducer is inserted. The endoscope 10 may also be an endoscope directed to a lower gastrointestinal tract. The endoscope 10 may also be a so-called rigid endoscope provided with a rigid insertion part 30. The endoscope 10 may also be a so-called industrial endoscope used for inspection of engine, pipework and so forth.

The endoscope cap 50 may be reusable. In such a case, the user visually checks the endoscope cap 50 removed from the insertion part 30 and, if it is not broken, reuses the cap 50 after performing a process such as cleaning. Since the opening end 56 of the endoscope cap 50 is wide open, a process such as cleaning may more easily be performed compared to the state where the endoscope cap 50 stays attached to the insertion part 30. Because of its small size, the endoscope cap 50 may easily be put into a sterile package for autoclave sterilization, for example.

The endoscope 10 may be provided with a fixing mechanism which fixes the elevator operation lever 21 at an arbitrary angle. The user is able to release his/her finger from the elevator operation lever 21 after elevating the treatment tool tip end 41 at a desired angle so as to concentrate on the operation of the bending knob 23 or the like.

Embodiment 2

The present embodiment relates to an endoscope 10 in which the third engagement part 29 is a projection. Portions common to those in Embodiment 1 will not be described here.

Figure 22:
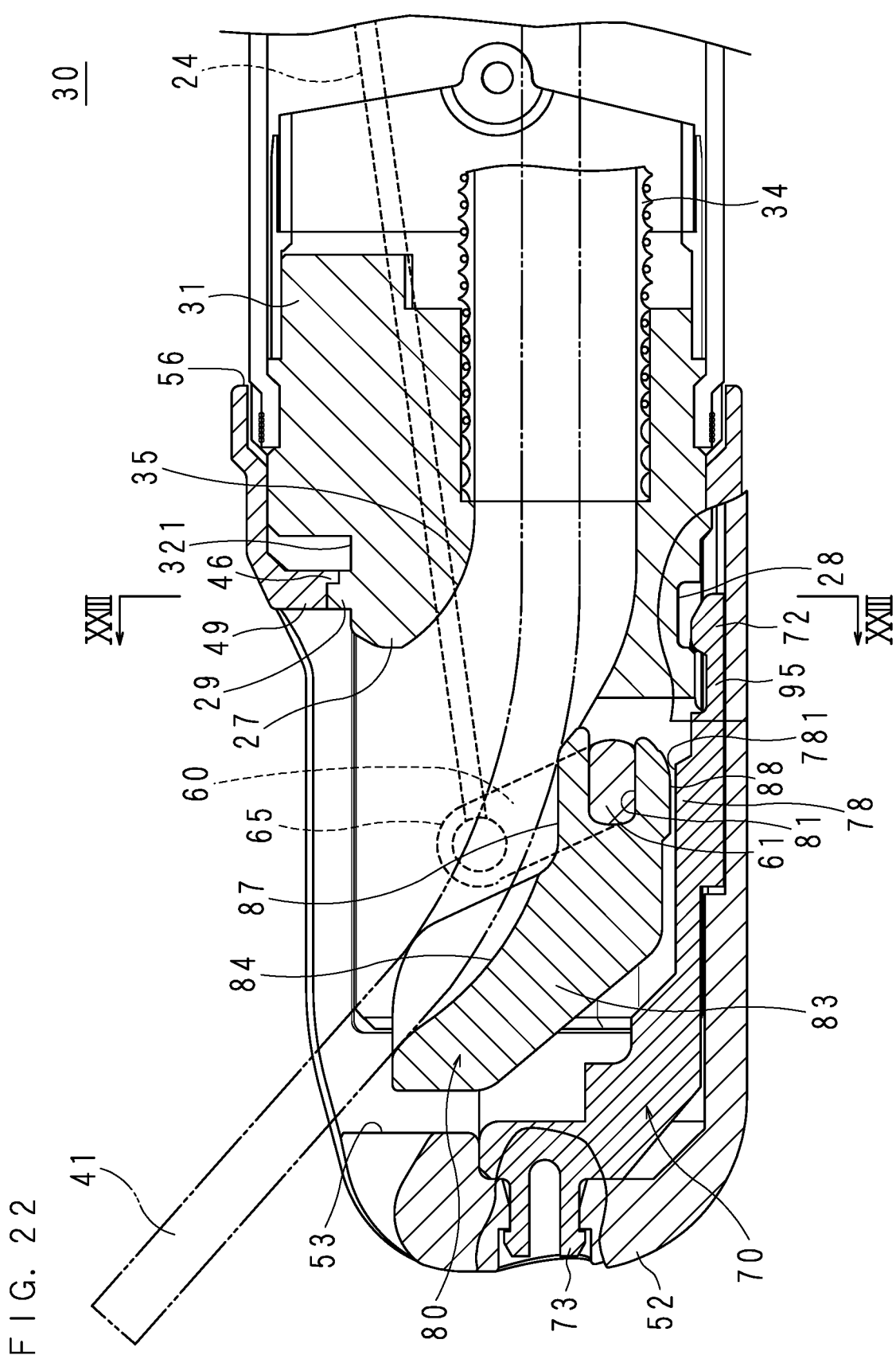
FIG. 22 is a section view of an insertion part according to Embodiment 2.
Figure 23:
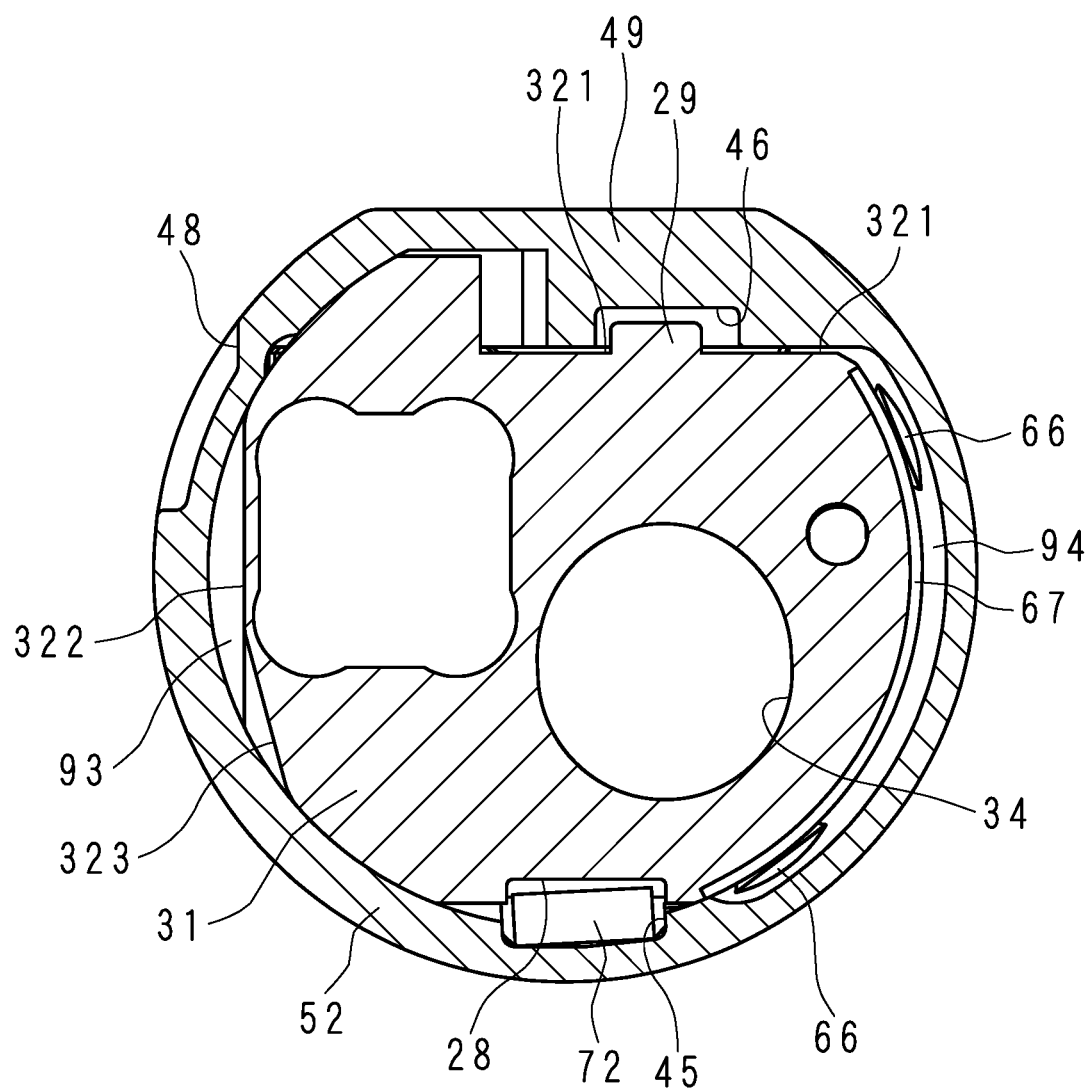
FIG. 23 is a section view of the insertion part taken along the line XXIII-XXIII in FIG. 22.

FIG. 22 is a section view of an insertion part 30 according to Embodiment 2. FIG. 22 illustrates a cross section, as in FIG. 19, which passes the elevator connection part 61 and which is along the longitudinal direction of the insertion part 30. FIG. 23 is a section view of the insertion part 30 taken along the line XXIII-XXIII in FIG. 22.

The third engagement part 29 is a projection which protrudes from the first planar part 321. The first engagement part 46 is a recess formed at the protrusion 49 on the window part 53 side. The first engagement part 46 is engaged with the third engagement part 29 of the distal end portion 31. Moreover, the second engagement part 72 is engaged with the fourth engagement part 28 as in Embodiment 1. The endoscope cap 50 is engaged with the distal end portion 31 at two opposed positions at the inner surface, so as to be fixed to the distal end of the insertion part 30.

The first engagement part 46 and the third engagement part 29 may employ any shapes that may be engaged with each other. The second engagement part 72 and the fourth engagement part 28 may also employ any shapes that may be engaged with each other.

Embodiment 3

The present embodiment relates to an endoscope 10 having an elevator connection part 61 tapered from the proximal side to the distal side along the insertion direction. Portions common to those in Embodiment 1 will not be described here.

Figure 24:
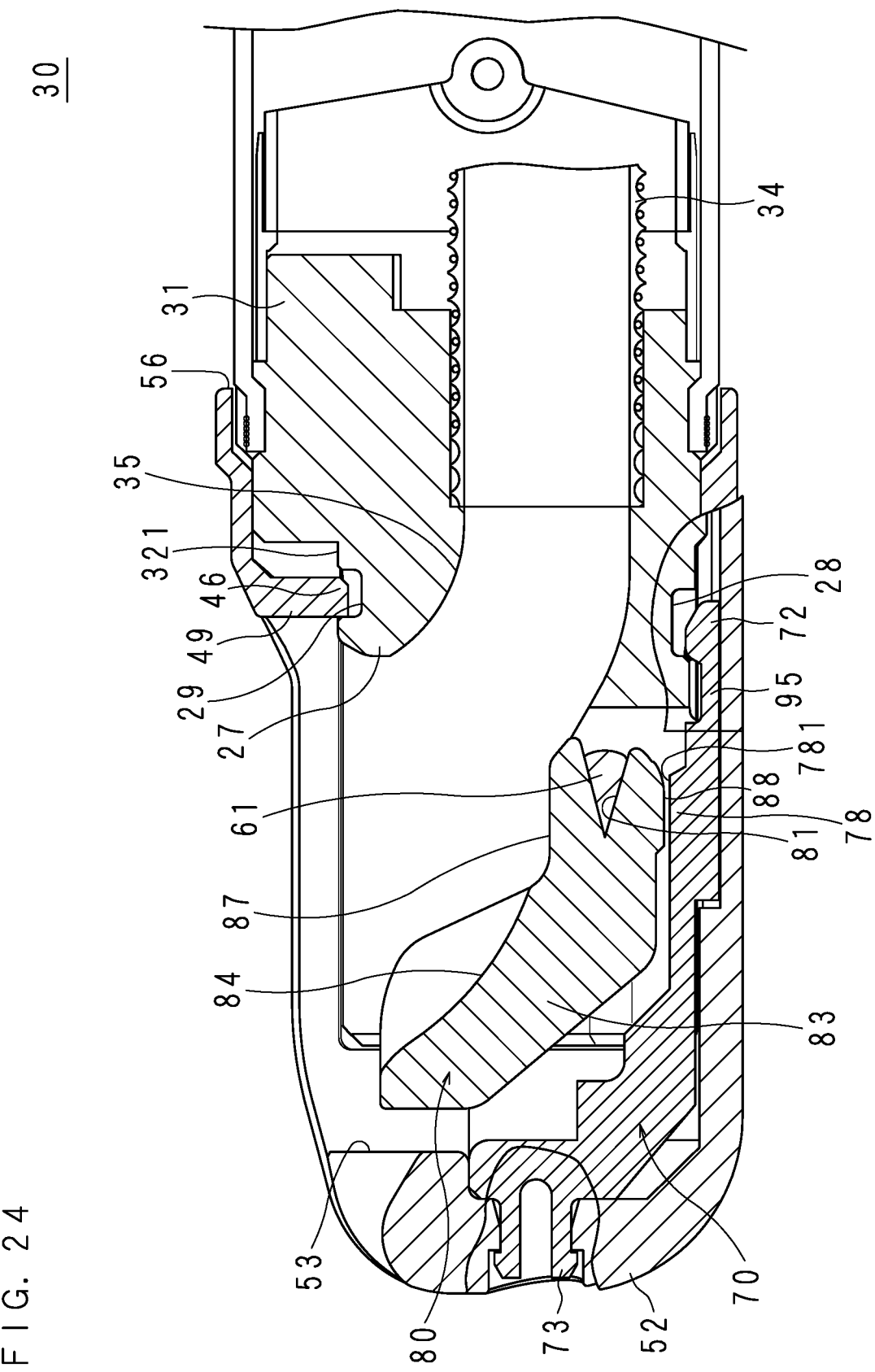
FIG. 24 is a section view of an insertion part according to Embodiment 3.

FIG. 24 is a section view of an insertion part 30 according to Embodiment 3. FIG. 24 illustrates a cross section, as in FIG. 19, which passes the elevator connection part 61 and which is along the longitudinal direction of the insertion part 30. As illustrated in FIG. 24, the elevator connection part 61 has a wedge shape with its distal side thinner than the proximal side. Moreover, the lever connection part 81 has a V shape expanding toward the proximal side.

According to the present embodiment, as the inlet of the lever connection part 81 is expanded while the elevator connection part 61 is tapered, the endoscope 10 in which the lever connection part 81 and the elevator connection part 61 may easily be engaged with each other even from the state where the elevator 80 has somewhat pivoted may be provided.

The elevator connection part 61 and the lever connection part 81 may employ any shapes that may be engaged with each other.

Embodiment 4

The present embodiment relates to an endoscope 10 having indices around the distal end of the insertion part 30 and at the endoscope cap 50, respectively. Portions common to those in Embodiment 1 will not be described here.

Figure 25:
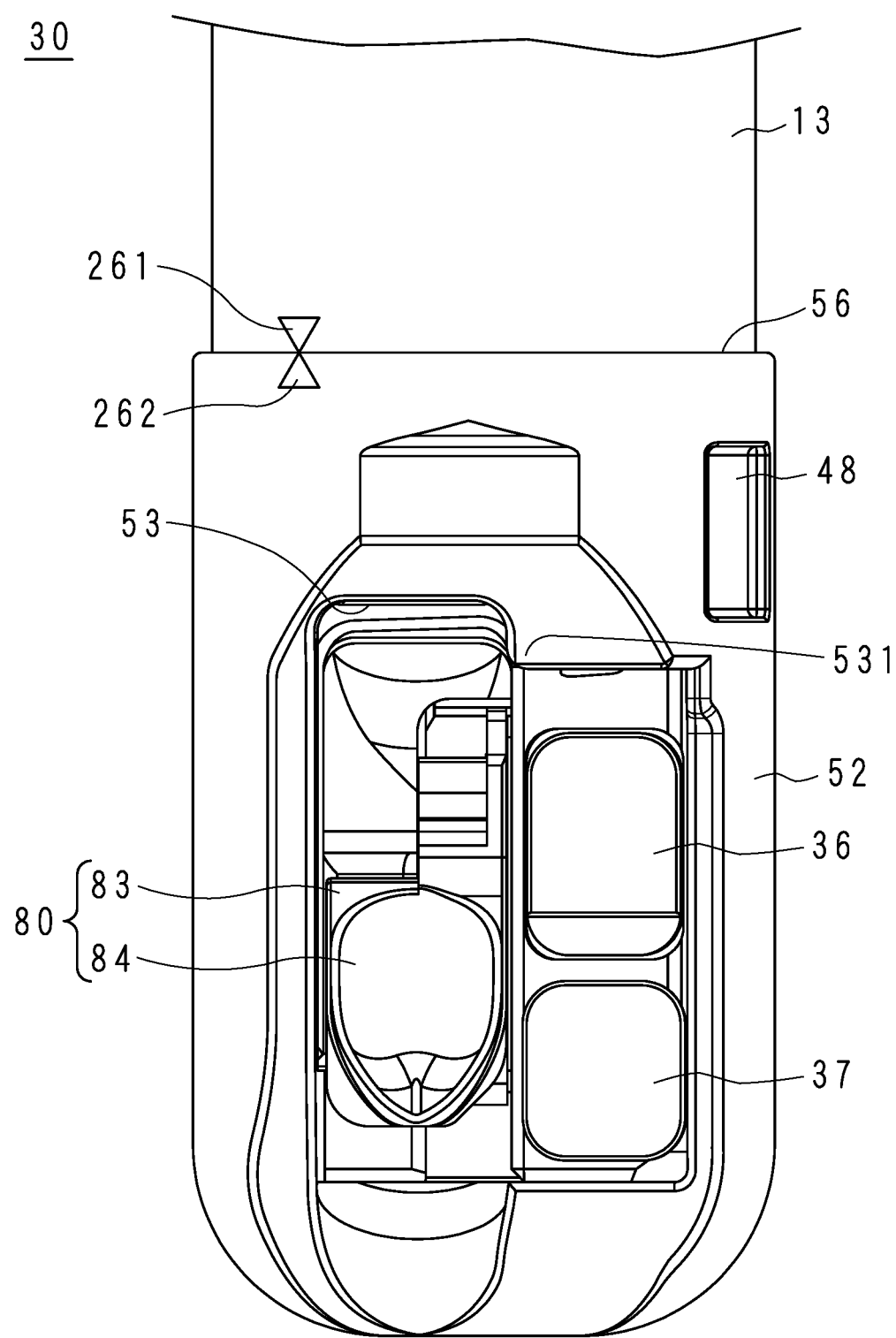
FIG. 25 is a front view of the distal end of an insertion part according to Embodiment 4.

FIG. 25 is a front view of the distal end of an insertion part 30 according to Embodiment 4. The insertion part 30 has a first index 261. The first index 261 is formed on the surface of a flexible tube which covers the surface of the bending section 13 by printing, laser machining or the like.

The cover 52 has a second index 262 in the vicinity of the opening end 56. The second index 262 is a recess or a projection integrally formed at the surface of the cover 52. The second index 262 may be formed on the surface of the cover 52 by printing, laser machining or the like. The second index 262 may be formed at or near the opening end 56 by a cutting work or the like.

According to the present embodiment, the user of the endoscope 10 is able to attach the endoscope cap 50 promptly and in proper orientation by pushing the endoscope cap 50 onto the distal end of the insertion part 30 while the first index 261 and the second index 262 are aligned in the circumferential direction. Furthermore, the user may visually checks if the first index 261 and the second index 262 are in close contact with each other as illustrated in FIG. 25, to confirm that the endoscope cap 50 is inserted all the way to a predetermined position.

The first index 261 and the second index 262 may have any shape, size and so forth.

Embodiment 5

The present embodiment relates to an endoscope 10 which uses the shape of the endoscope cap 50 itself in place of the second index 262. Portions common to those in Embodiment 4 will not be described here.

Figure 26:
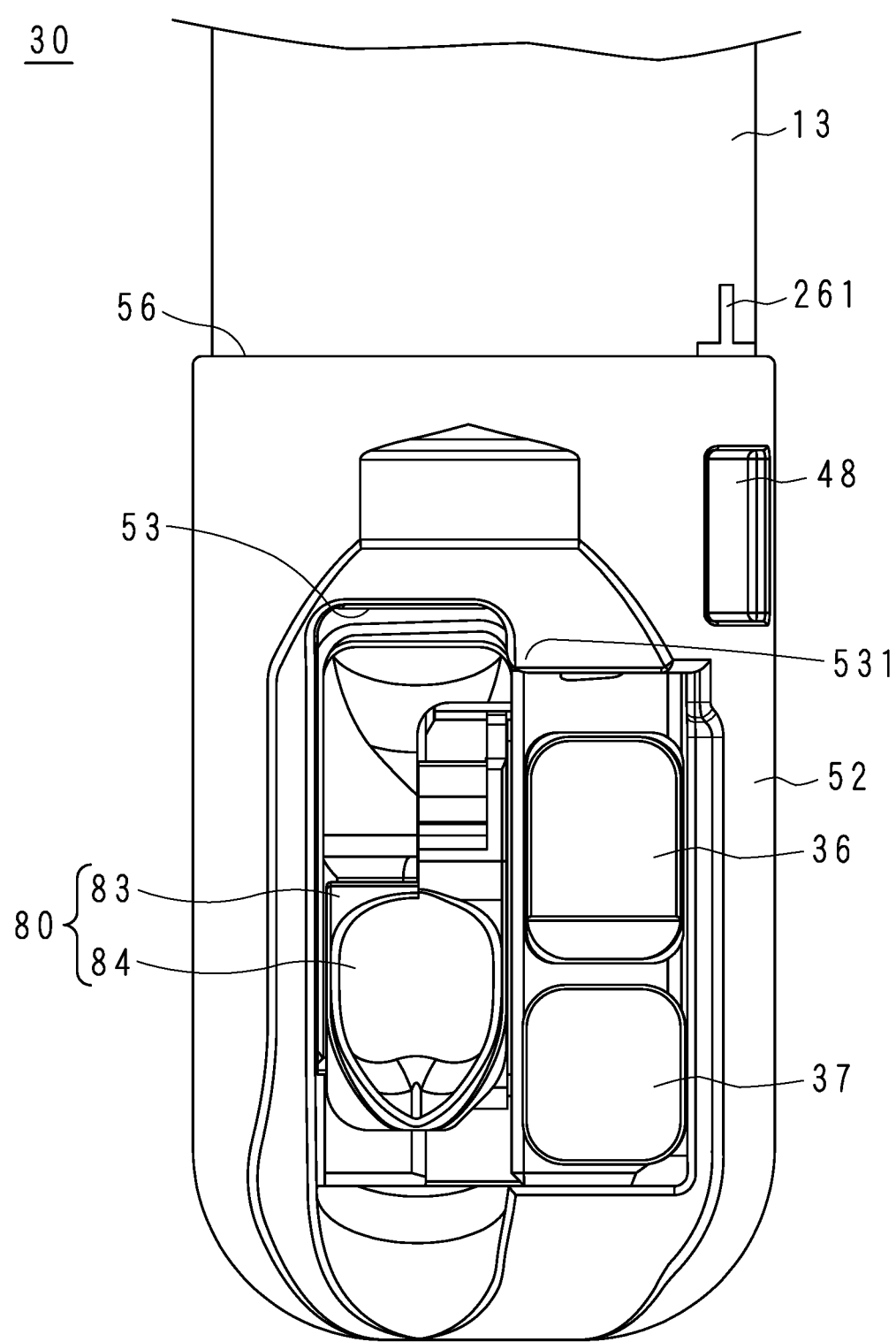
FIG. 26 is a front view of the distal end of an insertion part according to Embodiment 5.

FIG. 26 is a front view of the distal end of an insertion part 30 according to Embodiment 5. The insertion part 30 has a first index 261.

In the present embodiment, a concave part 48 formed at the surface of the cover 52 is used in place of the second index 262 in Embodiment 4.

According to the present embodiment, the user of the endoscope 10 is able to attach the endoscope cap 50 promptly and in proper orientation by pushing the endoscope cap 50 onto the distal end of the insertion part 30 while the first index 261 and the concave part 48 are aligned in the circumferential direction. Furthermore, the user may visually checks if the opening end 56 and the first index 261 are in close contact with each other as illustrated in FIG. 25, to confirm that the endoscope cap 50 is inserted all the way to a predetermined position.

The first index 261 may have any shape, size and so forth. An arbitrary portion of the cover 52, such as the edge of the window part 53, may be used in place of the second index 262.

The technical features (components) described in each example embodiment may be combined with one another, and such combinations may form new technical features.

It should be understood that the embodiments disclosed herein are illustrative and non-restrictive in every respect. Since the scope of the present disclosure is defined by the appended claims rather than by the description preceding them, all changes that fall within metes and bounds of the claims, or equivalence of such metes and bounds thereof are therefore intended to be embraced by the claims.

In relation to the embodiments including Embodiments 1 to 5 described above, the following clauses will further be disclosed.

1. An endoscope cap attachable to and detachable from an endoscope including a lever pivotally provided at a distal end of an insertion part of an endoscope and a pivot part causing the lever to pivot, comprising:
a bottomed cylindrical cover having an opening end which is attachable to and detachable from a distal end of an insertion part of the endoscope;
a first engagement part provided at an inner surface of a cylindrical part of the cover; and
an elevator having a lever connection part connected to the lever and fixed to an inside of the cover so as to be pivotable.

2. The endoscope cap according to clause 1, wherein the first engagement part is a projection protruding to the inside of the cover.

3. The endoscope cap according to clause 2, wherein
the cover has a window part opened at the cylindrical part, and
the projection is formed at a part closer to an opening end side compared to the window part.

4. The endoscope cap according to clause 3, wherein the projection is formed at an edge of the opening part on the opening end side.

5. The endoscope cap according to any one of clauses 2 to 4, wherein
the insertion part of the endoscope has a distal end provided with a concave third engagement part, and
the first engagement part is engaged with the third engagement part.

6. The endoscope cap according to any one of clauses 2 to 5, further comprising a second engagement part opposed to the first engagement part.

7. The endoscope cap according to clause 6, further comprising
a pedestal fixed to the inside of the cover and having an elevator attachment hole for pivotally fixing the elevator,
wherein the second engagement part is a projection formed at the pedestal.

8. The endoscope cap according to clause 7, wherein the first engagement part has an amount of protrusion larger than an amount of protrusion of the second engagement part.

9. The endoscope cap according to any one of clauses 6 to 8, wherein the first engagement part is formed closer to the opening end side compared to the second engagement part.

10. The endoscope cap according to any one of clauses 7 to 9, wherein
the insertion part of the endoscope has a distal end provided with a concave fourth engagement part, and
the second engagement part is engaged with the fourth engagement part.

11. The endoscope cap according to any one of clauses 5 to 10,
further comprising
a cavity formed between an inner surface of a cylindrical part of the cover and the insertion part when the insertion part is inserted into the cover,
wherein the first engagement part presses the cover from the outside of the cavity so as to release engagement with the insertion part.

12. The endoscope cap according to clause 1, wherein the first engagement part corresponds to a concave part located at an inner surface of the cover.

13. An endoscope, comprising:
a pivotable elevator connection part exposed to a surface of a distal end of an insertion part;
an endoscope cap including: a bottomed cylindrical cover that has an opening end and is capable of attaching and detaching the opening end to and from the insertion part; a first engagement part located at an inner surface of the cylindrical part of the cover; and an elevator that has a lever connection part connected to the elevator connection part and that is pivotally fixed to an inside of the cover;
a third engagement part provided at the insertion part and engaged with the first engagement part; and
a cavity formed between the inner surface of the cylindrical part of the cover and the insertion part.

14. The endoscope according to clause 13, wherein
the first engagement part is released from the third engagement part by pressing the cover from an outside of the cavity.

15. The endoscope according to clause 13 or 14, wherein
the elevator connection part protrudes from a hollow lever chamber protruding from a part of the distal end of the insertion part in an insertion direction,
the lever chamber is covered with a plate-like lever chamber lid, and
the cavity is provided between the lever chamber lid and the cover.

16. The endoscope according to clause 15, comprising
a fixing member fixing the lever chamber lid, wherein
the fixing member includes a head protruding from a surface of the lever chamber lid, and
the head is located inside the cavity.

17. The endoscope according to any one of clauses 13 to 16, wherein
the cavity is provided at two opposed positions across the insertion direction.

18. The endoscope according to any one of clauses 13 to 17, wherein the elevator connection part is thinner at a distal side compared to a proximal side along the insertion direction.

19. The endoscope according to any one of clauses 13 to 18, wherein
the distal end of the insertion part has a first index, and
the endoscope cap has a second index corresponding to the first index.

20. A method of detaching an endoscope cap, comprising:
gripping an insertion part of an endoscope having a pivotable elevator connection part exposed to a surface of the insertion part;
pressing the endoscope cap including: a bottomed cylindrical cover that has an opening end, is capable of attaching and detaching the opening end to and from the insertion part, and has a cavity between the cover and the distal end of the insertion part of the endoscope when attached; a first engagement part located at an inner surface of a cylindrical part of the cover; and an elevator that has a lever connection part connected to the elevator connection part and that is pivotally fixed to an inside of the cover, at two opposed positions outside the cylindrical part of the cover; and
pulling the endoscope cap toward a distal side along an insertion direction.

The invention claimed is:

1. An endoscope cap attachable to and detachable from an endoscope having a lever pivotally provided at a distal end of an insertion part of an endoscope and a pivot part causing the lever to pivot, the endoscope cap comprising:
a bottomed cylindrical cover having an opening end which is attachable to and detachable from the distal end of an insertion part of the endoscope;
a protrusion part with a plate shape configured to inwardly protrude from an inner surface of a cylindrical part of the cover;
a first engagement part with a rectangular-plate shape configured to further protrude from a part of an end surface of the protrusion part;
an elevator having a groove configured to engage with the lever and pivotally held at an inside of the cover;
a pedestal attached to the inside of the cover and having an elevator attachment hole for pivotally holding the elevator; and
a second engagement part that is opposed to the first engagement part and that is a projection provided at the pedestal.

2. The endoscope cap according to claim 1, wherein the first engagement part and the second engagement part protrude from an inner surface of a cylindrical part of the cover, the first engagement part protruding inwardly farther than the second engagement part does.

3. The endoscope cap according to claim 1,
wherein a cavity is formed between the inner surface of the cylindrical part of the cover and the insertion part when the insertion part is inserted into the cover, and
wherein the first engagement part is released from engagement with the insertion part by pressing the cover from an outside of the cavity.

4. An endoscope, comprising:
a pivotable shaft with a rectangular cross-section exposed to a surface of a distal end of an insertion part;
an endoscope cap including a bottomed cylindrical cover that has an opening end which is attachable to and detachable from the distal end of the insertion part, a protrusion part with a plate shape configured to inwardly protrude from an inner surface of a cylindrical part of the cover and a first engagement part with a rectangular-plate shape configured to further protrude from a part of an end surface of the protrusion part, and an elevator that has a groove configured to engage with the pivotable shaft and that is pivotally held at an inside of the cover; and
a third engagement part provided which is a recess having an opening larger than an end surface of the first engagement part and is provided at the insertion part and engaged with the first engagement part; and
a cavity formed between the inner surface of the cylindrical part of the cover and the insertion part.

5. The endoscope according to claim 4, wherein
the distal end of the insertion part has a first index, and
the endoscope cap has a second index corresponding to the first index.

6. The endoscope according to claim 4,
wherein the cavity is formed between the inner surface of the cylindrical part of the cover and the insertion part when the insertion part is inserted into the cover, and
wherein the first engagement part is released from engagement with the insertion part by pressing the cover from an outside of the cavity.

7. The endoscope according to claim 4, wherein the endoscope cap comprises a second engagement part opposed to the first engagement part.

8. The endoscope according to claim 7, wherein the endoscope cap comprises a pedestal attached to the inside of the cover and having an elevator attachment hole for pivotally holding the elevator,
wherein the second engagement part is a projection provided at the pedestal.

9. The endoscope according to claim 7, wherein the first and second engagement parts protrude inwardly from the inner surface of the cylindrical part of the cover,
the first engagement part protruding inwardly farther than the second engagement part does.

10. The endoscope according to claim 4, wherein a cavity is formed between the inner surface of the cylindrical part of the cover and the insertion part when the insertion part is inserted into the cover, and
wherein the first engagement part is released from engagement with the insertion part by pressing the cover from an outside of the cavity.

\* \* \* \* \*